US011960249B2

(12) United States Patent
Kim et al.

(10) Patent No.: US 11,960,249 B2
(45) Date of Patent: Apr. 16, 2024

(54) WEARABLE ELECTRONIC DEVICE WITH AN OPTICAL SENSOR MODULE INTEGRATED WITH A WIRELESS CHARGING MODULE

(71) Applicant: Samsung Electronics Co., Ltd., Gyeonggi-do (KR)

(72) Inventors: Taegyun Kim, Gyeonggi-do (KR); Junghyun Kang, Gyeonggi-do (KR); Kijung Kim, Gyeonggi-do (KR); Shinhun Moon, Gyeonggi-do (KR); Seunghyun Cho, Gyeonggi-do (KR); Seongho Hong, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 111 days.

(21) Appl. No.: 17/708,295

(22) Filed: Mar. 30, 2022

(65) Prior Publication Data

US 2022/0330439 A1    Oct. 13, 2022

Related U.S. Application Data

(63) Continuation of application No. PCT/KR2022/003521, filed on Mar. 14, 2022.

(30) Foreign Application Priority Data

Apr. 1, 2021    (KR) .................. 10-2021-0042589

(51) Int. Cl.
*G04G 19/00*    (2006.01)
*A61B 5/00*    (2006.01)
(Continued)

(52) U.S. Cl.
CPC ............ *G04G 19/00* (2013.01); *G04G 9/007* (2013.01); *G04G 21/025* (2013.01);
(Continued)

(58) Field of Classification Search
CPC ..... G04C 10/00; A61B 5/02416; A61B 5/681; A61B 5/02438; A61B 5/256; A61B 5/28;
(Continued)

(56) References Cited

U.S. PATENT DOCUMENTS 9,048,396 B2    6/2015    Lowes et al.
9,818,919 B2    11/2017    Lowes et al.
(Continued)

FOREIGN PATENT DOCUMENTS

CN    104997503 A    10/2015
CN    212414966 U    1/2021
(Continued)

OTHER PUBLICATIONS

International Search Report dated Jun. 28, 2022.

*Primary Examiner* — Jennifer D Bennett
(74) *Attorney, Agent, or Firm* — Cha & Reiter, LLC

(57) ABSTRACT

A wearable electronic device, for example a smart watch, has an optical sensor module disposed near a side of the device meant to face the wearer. The device also includes a wireless charging module. The optical sensor and wireless charging modules are at least partially integrated together via a flexible printed circuit board ("FPCB") which is connected to both modules. The wireless charging module surrounds the FPCB of the optical sensor module, thus allowing a reduction in thickness of the wearable device and further allowing simplification in a process of assembly of the device.

19 Claims, 13 Drawing Sheets

(51) Int. Cl.
  *A61B 5/024* (2006.01)
  *G04G 9/00* (2006.01)
  *G04G 21/02* (2010.01)
  *H02J 7/00* (2006.01)
  *H02J 50/00* (2016.01)
  *H02J 50/10* (2016.01)
  *H05K 1/02* (2006.01)
  *H05K 5/00* (2006.01)

(52) U.S. Cl.
  CPC .......... *H02J 7/0042* (2013.01); *H02J 50/005* (2020.01); *H05K 1/028* (2013.01); *H05K 5/0026* (2013.01); *A61B 5/02416* (2013.01); *A61B 5/681* (2013.01); *H02J 50/10* (2016.02); *H05K 2201/10106* (2013.01); *H05K 2201/10151* (2013.01)

(58) Field of Classification Search
  CPC .. A61B 2560/02414; A61B 2560/0443; A61B 2562/0233; A61B 2562/166; H05K 5/0026; H05K 1/028; H05K 2201/10106; H05K 2201/10151; H05K 1/147; H05K 2201/10098; H05K 1/189; G04G 9/007; G04G 19/00; G04G 21/025; G04G 17/00; G04G 17/04; G04G 17/08; G04G 21/04; H02J 7/0042; H02J 50/005; H02J 50/10; H02J 50/12
  See application file for complete search history.

(56) References Cited

U.S. PATENT DOCUMENTS

| | | | |
|---|---|---|---|
| 9,865,780 | B2 | 1/2018 | Lowes et al. |
| 10,129,377 | B2 | 11/2018 | Evans, V |
| 10,381,881 | B2 | 8/2019 | Wittenberg et al. |
| 10,485,478 | B1 | 11/2019 | Mirov et al. |
| 10,878,959 | B1 | 12/2020 | Reykhert |
| 10,993,661 | B1 | 5/2021 | Mirov et al. |
| 11,011,943 | B2 | 5/2021 | Wittenberg et al. |
| 11,024,423 | B2 | 6/2021 | Reykhert |
| 2004/0176669 | A1* | 9/2004 | Colvin, Jr. ........... G01N 21/648 128/903 |
| 2013/0328073 | A1 | 12/2013 | Lowes et al. |
| 2018/0090975 | A1* | 3/2018 | Lee ....................... H05K 5/0017 |
| 2018/0132738 | A1* | 5/2018 | Choi ................... H01M 10/425 |
| 2018/0191879 | A1 | 7/2018 | Evans, V |
| 2019/0246922 | A1* | 8/2019 | Matsuo .............. A61B 5/02438 |
| 2020/0260972 | A1 | 8/2020 | Han et al. |
| 2020/0323489 | A1 | 10/2020 | Kim et al. |
| 2021/0241900 | A1 | 8/2021 | Reykhert |
| 2022/0151554 | A1 | 5/2022 | Jang et al. |

FOREIGN PATENT DOCUMENTS

| | | |
|---|---|---|
| KR | 10-2019-0027341 A | 3/2019 |
| KR | 10-2020-0100487 A | 8/2020 |
| KR | 10-2020-0120407 A | 10/2020 |
| KR | 10-2021-0015250 A | 2/2021 |

* cited by examiner

WEARABLE ELECTRONIC DEVICE WITH AN OPTICAL SENSOR MODULE INTEGRATED WITH A WIRELESS CHARGING MODULE

CROSS-REFERENCE TO RELATED APPLICATION(S)

This application is a Continuation of and claims priority under 35 U.S.C. § 120 to PCT International Application No. PCT/KR2022/003521, which was filed on Mar. 14, 2022, which claims priority to Korean Patent Application No. 10-2021-0042589, filed on Apr. 1, 2021 in the Korean Intellectual Property Office, the disclosures of which are herein incorporated by reference.

TECHNICAL FIELD

Certain embodiments of the disclosure described herein relate to an electronic device including a module assembly in an integrated form.

BACKGROUND

With the increased usage of portable devices and smartphones, there has been increased usage of interworking smart devices, such as smart watches, which are usable independently or in conjunction with smartphones. The interworking smart devices are connectable to the smartphones using wired or wireless communication, and may provide a diversity of additional functionality beyond the smartphone. Because of their convenience, widespread acceptance of their usage is on the rise.

Wearable electronic devices in particular, due to their very nature, may be kept in contact with the human body for a long amount of time. For example, a diversity of user biometrics may be monitored; e.g., such as photoplethysmography or "PPG," sleep characteristics, skin temperature, heart rate or electrocardiogram readings, etc. depending on the sensor utilized. The detected biometrics may be used in health-related functionality for the user. Wearable devices are often limited due to size requirements for the same. To provide desirable functions through the wearable electronic device, a variety of electronic components are disposed within the electronic device. Due to the limitations of space, it is important to design the components to be placed in economically efficient arrangements and positions.

For example, the wearable electronic device may include a biosensor module and a wireless charging module. The biosensor module may be implemented in a stacked arrangement of components. However, if so, the thickness of the electronic device may increase as a result. Furthermore, because of the presence of a step between a circuit board (an FPCB) of the biosensor module and the wireless charging module (e.g., or a coil), there may be design limitations for the connecting structure.

SUMMARY

Certain embodiments of the disclosure provide an electronic device in which the thickness of the overall device may be reduced, and an assembly process for the same may be simplified, by integrally forming an optical sensor module and a wireless charging module.

An electronic device according to an embodiment of the disclosure includes a front plate, a back plate facing the front plate, and a side frame surrounding a space defined between the front plate and the back plate, a circuit board disposed within the housing, a module assembly disposed between the circuit board and the back plate, and electrically connected with the circuit board, wherein the module assembly includes an optical sensor module including a flexible printed circuit board (FPCB) including a first surface and a second surface facing away from the first surface, a light emitting part disposed on the first surface of the FPCB, and a light receiving part disposed on the first surface spaced apart from the light emitting part, and a wireless charging module surrounding the FPCB of the optical sensor module, and at least partially coupled to the FPCB so as to be integrated with the FPCB.

A wearable electronic device according to an embodiment of the disclosure includes a housing including a housing including a front surface facing a first direction, a rear surface facing a second direction opposite to the first direction, and a side surface surrounding a space between the front surface and the rear surface, a display disposed in the housing and visibly exposed through the front surface, a circuit board disposed in the housing, a module assembly disposed between the circuit board and the rear surface, and electrically connected with the circuit board, and a connecting member connecting the module assembly and the circuit board, wherein the module assembly includes an optical sensor module including a flexible printed circuit board (FPCB) including a first surface facing the second direction and a second surface facing the first direction, a light emitting part disposed on the first surface of the FPCB, and a light receiving part disposed on the first surface so as to be spaced apart from the light emitting part, and a wireless charging module surrounding the FPCB and at least partially coupled to the FPCB so as to be integrated with the FPCB, wherein the optical sensor module is configured to detect a biometric signal of an external object as the light emitting part emits light in the second direction, and the light receiving part receives emitted light reflecting off the external object, when the external object is in contact with the rear surface of the wearable electronic device.

According to the certain embodiments of the disclosure, the optical sensor module may be implemented as a "chip-on-board" (COB) sensor. Accordingly, the optical sensor and wireless charging modules may be aligned and integrally connected.

Furthermore, according to the certain embodiments of the disclosure, the wireless charging module and the optical sensor module may be integrally formed with one another, and may both be electrically connected to the circuit board using the connecting member. Accordingly, the electronic device may benefit from increased interior space for arranging other components therein, and manufacturing costs may be reduced.

Moreover, according to the certain embodiments of the disclosure, the module assembly and the cover may be coupled in an integrally modularized state. Accordingly, the assembly process of the electronic device may be simplified, which may reduce the potential formation of defects in the manufacturing process.

In addition, the disclosure may provide other advantageous effects that may be directly or indirectly recognized.

BRIEF DESCRIPTION OF THE DRAWINGS

In the following description made with respect to the accompanying drawings, similar components will be assigned with similar reference numerals.

DETAILED DESCRIPTION

Hereinafter, certain embodiments of the disclosure may be described with reference to accompanying drawings. Accordingly, those of ordinary skill in the art will recognize that modification, equivalent, and/or alternative on the certain embodiments described herein can be variously made without departing from the scope of the disclosure.

Figure 1:
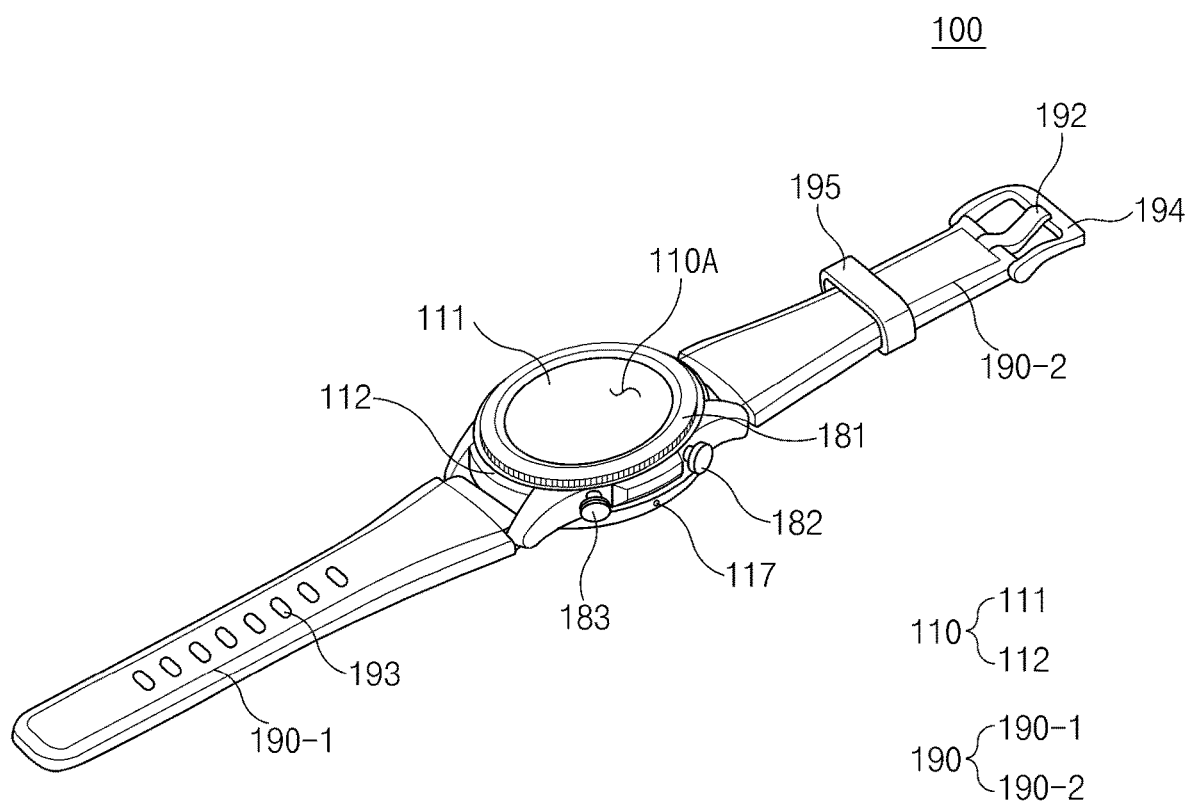
FIG. 1 is a front perspective view of an electronic device according to an embodiment.
Figure 2:
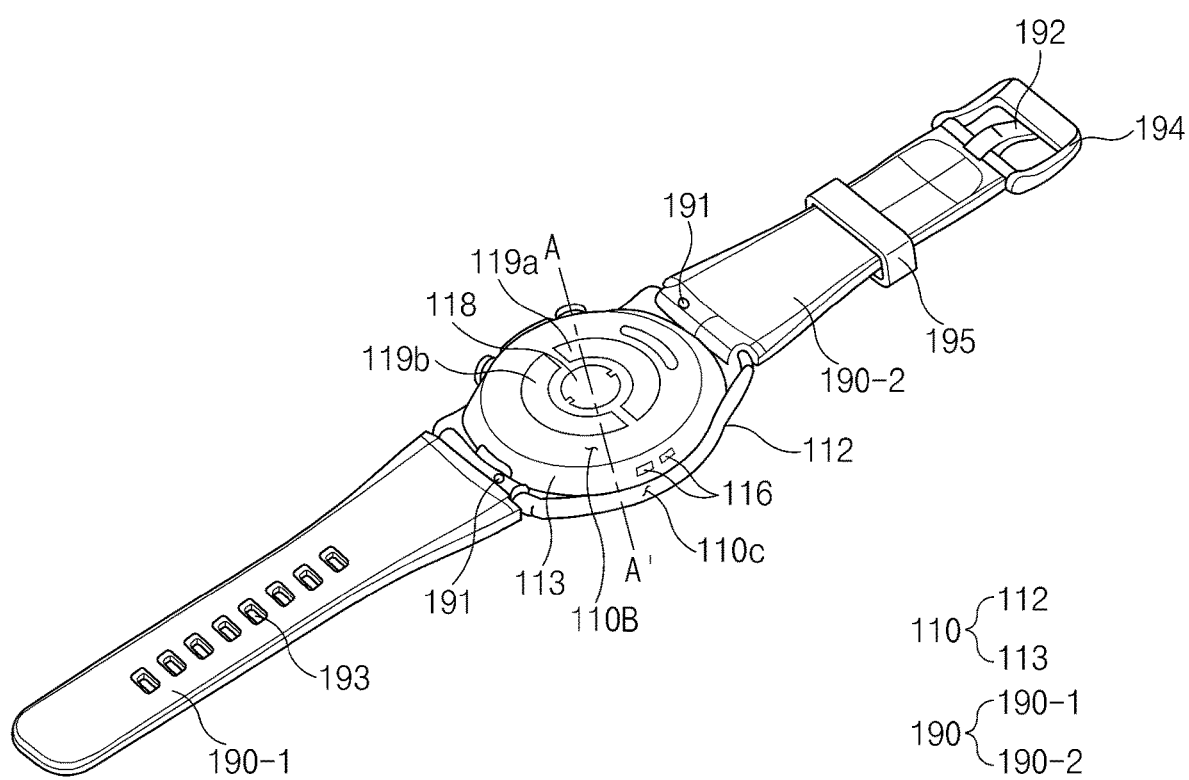
FIG. 2 is a rear perspective view of the electronic device according to an embodiment.

FIG. 1 is a front perspective view of an electronic device according to an embodiment. FIG. 2 is a rear perspective view of the electronic device according to an embodiment.

Referring to FIGS. 1 and 2, the electronic device 100 according to an embodiment may include a housing 110, audio modules 116 and 117, sensor modules 118, 119*a*, and 119*b*, key input devices 181, 182, and 183, and/or a fastening member 190.

The electronic device 100 according to an embodiment may be a wearable electronic device. For example, the electronic device 100 may be a watch type electronic device (e.g., a smart watch) wearable on a part (e.g., a wrist or an ankle) of a user's body. However, the electronic device according to certain embodiments of the disclosure is not limited to the illustrated embodiment.

In an embodiment, the housing 110 may form at least part of the exterior of the electronic device 100. The housing 110 may include a front plate 111, a side frame 112 (e.g., a side bezel or a side member), and a back plate 113. The front plate 111, the side frame 112, and the back plate 113 may be coupled together. For example, through a coupling structure of the front plate 111, the side frame 112, and the back plate 113, the housing 110 may form an inner space in which other components (e.g., a display 120, a bracket 130, a circuit board 140, and/or a battery 185 of FIGS. 3 and 4) of the electronic device 100 are accommodated.

In an embodiment, the housing 110 may include a front surface 110A, a rear surface 110B facing away from the front surface 110A, and a side surface 110C surrounding a space between the front surface 110A and the rear surface 110B. For example, the front surface 110A may be included in the front plate 111, the side surface 110C may be included in the side frame 112, and the rear surface 110B may be included in the back plate 113. According to certain embodiments, the housing 110 may be understood to refer to a structure that forms some of the front surface 110A, the rear surface 110B, and the side surface 110C.

In an embodiment, the front plate 111 may form at least part of the front surface 110A of the housing 110. For example, at least part of the front surface 110A may be formed by the substantially transparent front plate 111. The front plate 111 may be formed of a glass plate including various coating layers, or a polymer plate.

In an embodiment, the back plate 113 may form at least part of the rear surface 110B of the housing 110. For example, the rear surface 110B may be formed by the substantially opaque back plate 113. The back plate 113 may be formed of coated or colored glass, ceramic, polymer, metal (e.g., aluminum, stainless steel (STS), or magnesium), or a combination of at least two thereof. In certain embodiments, at least a partial area of the back plate 113 may be formed to be substantially transparent such that a portion of the sensor module 118 is visually exposed.

In an embodiment, the side frame 112 may form at least part of the side surface 110C of the housing 110. For example, the side surface 110C may be formed by the side frame 112 coupled with the front plate 111 and the back plate 113. The side frame 112 may contain metal and/or polymer. In certain embodiments, the side frame 112 may be integrally formed with the back plate 113. For example, the back plate 113 and the side frame 112 may be integrally formed with each other and may contain the same material (e.g., a metallic material such as aluminum).

The electronic device 100 according to an embodiment may include a display (e.g., the display 120 of FIGS. 3 to 5) disposed in the housing 110 and visually exposed outside the electronic device 100. For example, at least part of the display 120 may be visually exposed on the front surface 110A of the housing 110 through the front plate 111 formed to be substantially transparent. The display 120 may be formed in a form corresponding to the form of the front plate 111. For example, the display 120 may be formed in various forms such as a circular shape, an oval shape, or a polygonal shape. The display 120 may be combined with, or disposed adjacent to, touch detection circuitry, a pressure sensor capable of measuring the intensity (pressure) of a touch, and/or a fingerprint sensor.

In an embodiment, the audio modules 116 and 117 may include the microphone hole and the speaker hole. For example, a microphone for obtaining an external sound may be disposed in the microphone hole. In certain embodiments, the electronic device 100 may include a plurality of microphones to sense sounds in various directions. For example, a speaker for outputting a sound to the outside may be disposed in the speaker hole and may be used as an external speaker and a receiver for telephone call. In certain embodiments, the speaker hole and the microphone hole may be implemented as a single hole. Alternatively, the electronic device 100 may be configured such that a speaker is included without the speaker hole (e.g., a piezoelectric speaker).

In an embodiment, the sensor modules 118, 119*a*, and 119*b* may generate an electrical signal or a data value that corresponds to an operational state inside the electronic device 100 or an environmental state external to the electronic device 100.

In an embodiment, the sensor modules 118, 119a, and 119b may include the first biosensor module 118 (e.g., an optical sensor module 160 of FIGS. 4 to 8) exposed on the rear surface 110B of the housing 110. A biometric signal sensed through the first biosensor module 118 (e.g., a heart rate monitor (HRM) sensor) may be a biometric signal related to a heart rate. For example, the first biosensor module 118 may be disposed in the housing 110, and at least part of the first biosensor module 118 may be visually exposed on the rear surface 110B of the housing 110 through a partial area of the back plate 113.

In an embodiment, the sensor modules 118, 119a, and 119b may include the second biosensor module 119a and 119b disposed on the rear surface 110B of the housing 110. A biometric signal sensed through the second biosensor module 119a and 119b (e.g., an electrocardiogram (ECG) sensor) may be a biometric signal related to an electrocardiogram. For example, the second biosensor module 119a and 119b may include the first electrode area 119a and the second electrode area 119b that are formed of a conductive material, and the first electrode area 119a and the second electrode area 119b may make contact with the user's body. The second biosensor module 119a and 119b may be configured to obtain an electrical signal from a part of the user's body through the first electrode area 119a and the second electrode area 119b and detect a biometrical signal of the user based on the obtained electrical signal.

In certain embodiments, the electronic device 100 may further include another sensor module, for example, at least one of a gesture sensor, a gyro sensor, an atmospheric pressure sensor, a magnetic sensor, an acceleration sensor, a grip sensor, a color sensor, an infrared (IR) sensor, a biosensor, a temperature sensor, a humidity sensor, or an illuminance sensor.

In an embodiment, the key input devices 181, 182, and 183 may include the wheel member 181 (e.g., a wheel key or a rotary bezel) disposed on the front surface 110A of the housing 110 and rotatable in at least one direction and/or the button members 182 and 183 (e.g., side keys) disposed on the side surface 110C of the housing 110.

In an embodiment, the wheel member 181 may have a form (e.g., a circular frame) corresponding to the form of the front plate 111. For example, the wheel member 181 may be rotated by a user operation to receive user inputs for implementing various functions of the electronic device 100.

In an embodiment, the button members 182 and 183 may be rotated and/or pushed by a user operation to receive user inputs for implementing various functions of the electronic device 100. In an embodiment, the button members 182 and 183 may include the first button member 182 and the second button member 183. In certain embodiments, at least one of the first button member 182 or the second button member 183 may be formed of an electrode button capable of detecting a biometric signal (e.g., an electrocardiogram) of the user as a part (e.g., a finger) of the user's body makes contact with the electrode button.

In certain embodiments, the electronic device 100 may not include all or some of the above-described key input devices 181, 182, and 183, and the key input devices not included may be implemented in a different form, for example, the form of a soft key on the display 120.

In an embodiment, the electronic device 100 may be detachably worn on a part (e.g., a wrist or an ankle) of the user's body by the fastening member 190. For example, the fastening member 190 may be connected to at least part of the housing 110 and may be configured to be detachably fastened in the state of surrounding a part of the user's body. For example, the fastening member 190 may include a first fastening member 190-1 and a second fastening member 190-2 that are coupled to opposite sides of the housing 110, respectively. The first fastening member 190-1 and the second fastening member 190-2 may be connected with or separated from each other.

In an embodiment, the fastening member 190 may be formed in a band or strap form to surround a part of the user's body. For example, the fastening member 190 may be formed of woven fabric, leather, rubber, urethane, metal, ceramic, or a combination of at least two of the aforementioned materials and may be implemented in an integrated form or with a plurality of unit links that are movable relative to each other.

In an embodiment, the fastening member 190 may be detachably connected to the housing 110. For example, the fastening member 190 may be detachably connected to at least a partial area of the housing 110 by a locking member 191. According to certain embodiments of the disclosure, the electronic device 100 may include various types of fastening members 190, and the fastening members 190 may be replaced depending on the user's taste and/or preference.

In an embodiment, the fastening member 190 may include a fixing member 192, fixing-member fastening holes 193, a band guide member 194, and/or a band fixing ring 195. For example, the fixing member 192 may be configured to fix the housing 110 and the fastening member 190 to a part (e.g., a wrist or an ankle) of the user's body. The fixing-member fastening holes 193 may fix the housing 110 and the fastening member 190 to the part of the user's body to correspond to the fixing member 192. The band guide member 194 may be configured to restrict a movement range of the fixing member 192 when the fixing member 192 is fastened to one of the fixing-member fastening holes 193. Accordingly, the fastening member 190 may be closely fastened around the part of the user's body. The band fixing ring 195 may restrict a movement range of the fastening member 190 in the state in which the fixing member 192 is fastened to one of the fixing-member fastening holes 193.

In certain embodiments, the electronic device 100 may not include at least one component (e.g., the key input devices 181, 182, and 183 or the sensor modules 118, 119a, and 119b) among the components illustrated in FIGS. 1 and 2, or may additionally include other component(s). For example, the electronic device 100 may further include a connector hole (not illustrated). The connector hole (not illustrated) may accommodate a connector (e.g., a USB connector) for transmitting and/or receiving power and/or data with an external electronic device, or may accommodate a connector (e.g., an earphone connector) for transmitting and/or receiving an audio signal with an external electronic device.

Figure 3:
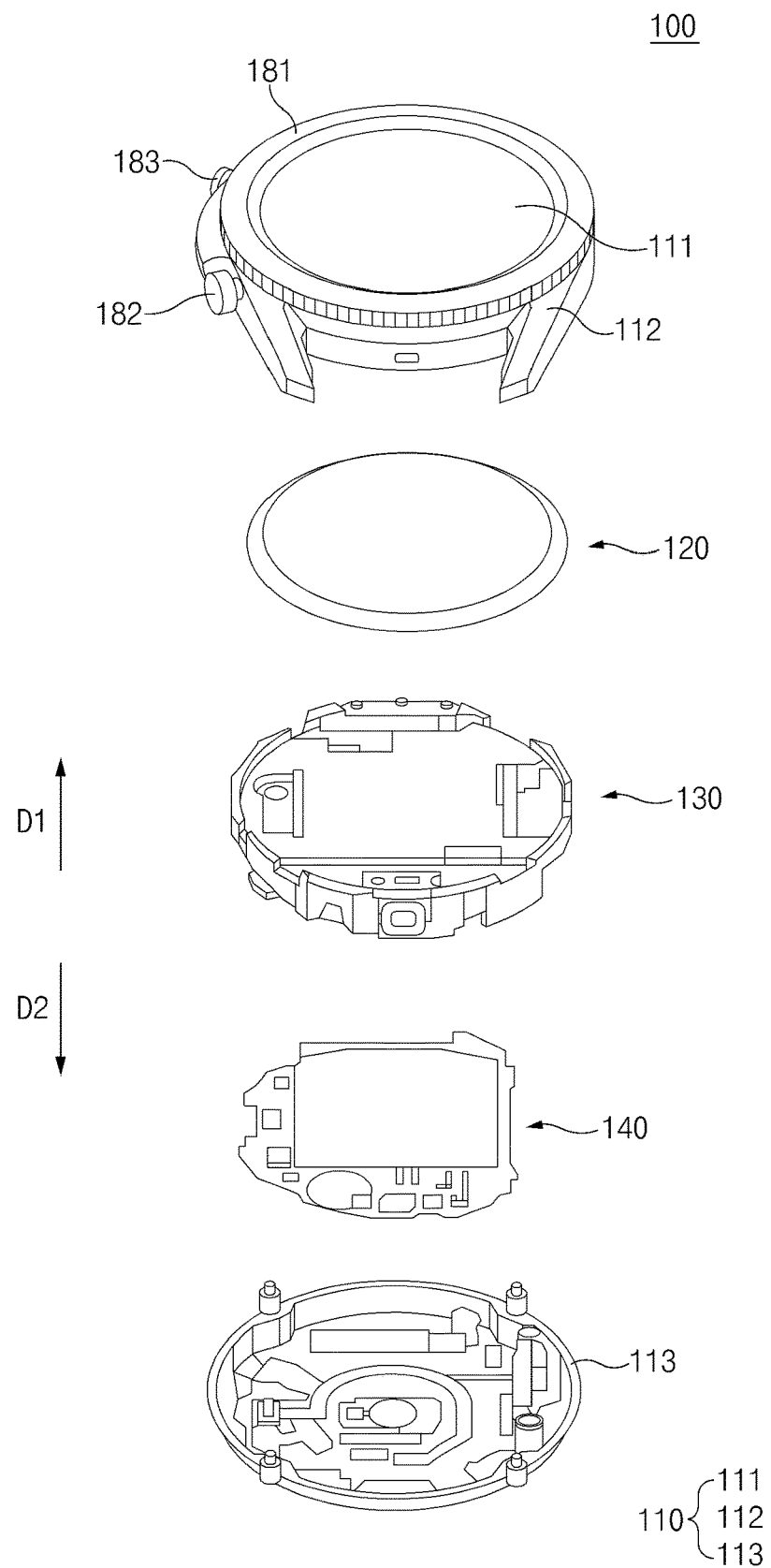
FIG. 3 is an exploded perspective view of the electronic device according to an embodiment.
Figure 4:
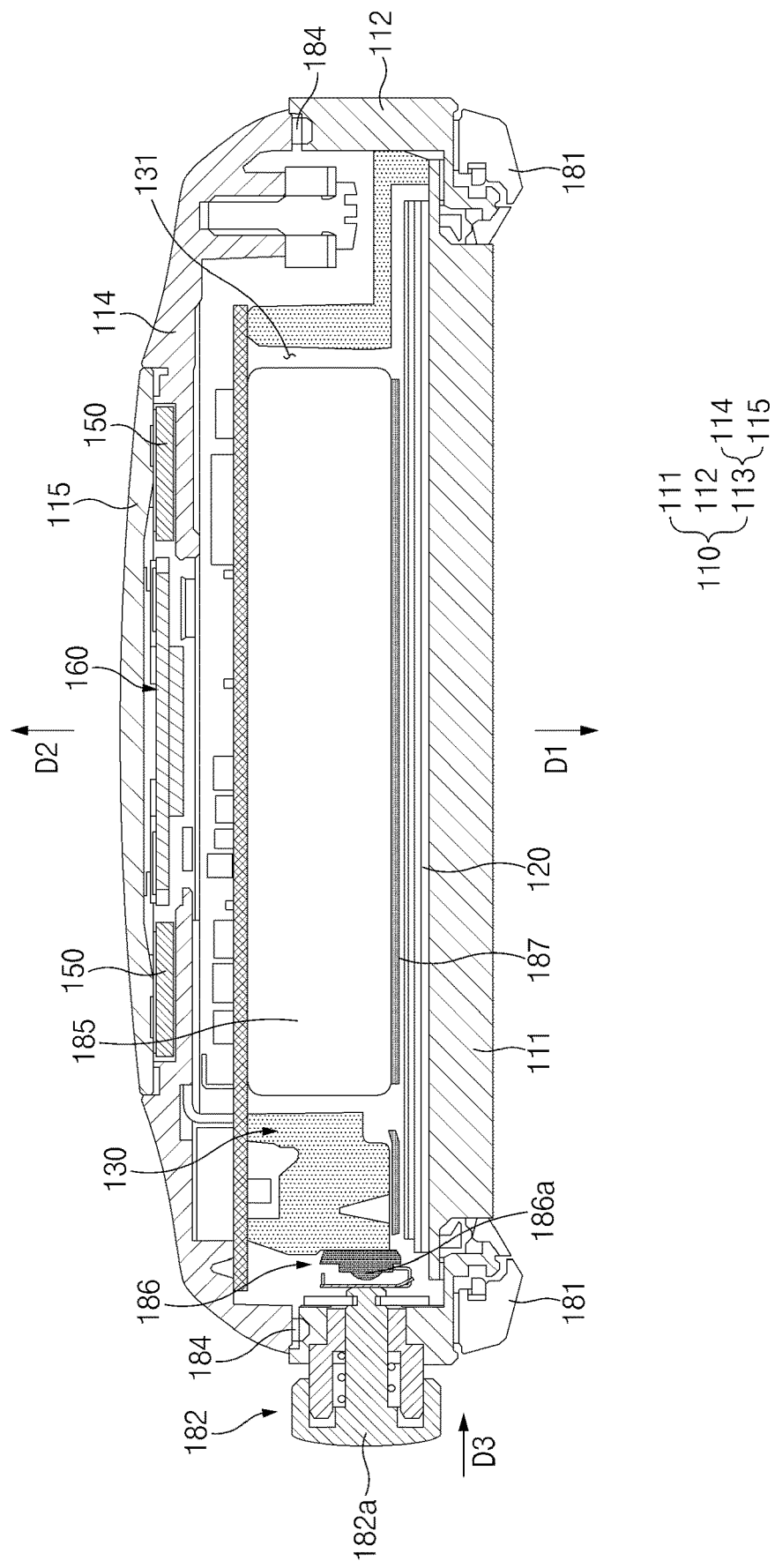
FIG. 4 is a sectional view of the electronic device according to the embodiment.

FIG. 3 is an exploded perspective view of the electronic device according to an embodiment. FIG. 4 is a sectional view of the electronic device according to the embodiment.

FIG. 4 is a sectional view of the electronic device taken along line A-A' illustrated in FIG. 2.

Referring to FIGS. 3 and 4, the electronic device 100 according to an embodiment may include the housing 110, the display 120, the bracket 130, the circuit board 140, a wireless charging module 150, the optical sensor module 160 (e.g., the first biosensor module 118 of FIG. 2), the wheel member 181, the button members 182 and 183, a sealing member 184, the battery 185, or a contact member 186.

FIGS. 3 and 4 may be views in which the fastening member (e.g., the fastening member 190 of FIGS. 1 and 2) of the electronic device 100 is omitted. Some of the components of the electronic device 100 illustrated in FIGS. 3 and 4 may be identical or similar to the components of the electronic device 100 illustrated in FIGS. 1 and 2, and repetitive descriptions will hereinafter be omitted.

In an embodiment, the housing 110 may include the front plate 111, the side frame 112, and the back plate 113. For example, the display 120, the bracket 130, the circuit board 140, the wireless charging module 150, a sensor module (e.g., the optical sensor module 160), and/or the battery 185 may be accommodated in an inner space formed by a coupling of the front plate 111, the side frame 112, and the back plate 113.

According to certain embodiments, the sensor module may be a sensor module for measuring a biometric signal of the user and may include, for example, the optical sensor module 160 (e.g., a PPG sensor module) or a non-optical sensor module (e.g., an ECG sensor module).

In an embodiment, the side frame 112 may include an opening area (not illustrated), and the front plate 111 may be exposed through the opening area in a first direction D1. For example, the front plate 111 may be coupled with the side frame 112 such that at least part of the front plate 111 is located in the opening area. The back plate 113 may be coupled to the side frame 112 to face one surface (e.g., the surface facing a second direction D2) of the front plate 111.

In an embodiment, the back plate 113 may include a rear case 114 coupled to the side frame 112 and a cover 115 coupled to the rear case 114. For example, the back plate 113 may be formed by a coupling of the rear case 114 and the cover 115. An outer surface of the rear case 114 and an outer surface of the cover 115 may form at least part of the rear surface of the electronic device 100. For example, the cover 115 may form the rear surface of the electronic device 100 together with the rear case 114 and may be attached to at least part of the rear case 114.

In an embodiment, the back plate 113 may support the wireless charging module 150 and the optical sensor module 160. For example, the back plate 113 may be configured such that the wireless charging module 150 and the optical sensor module 160 are located in a space between the rear case 114 and the cover 115 (e.g., refer to FIGS. 5 and 6). In certain embodiments, the wireless charging module 150 and the optical sensor module 160 may be attached to the cover 115. For example, the wireless charging module 150, the optical sensor module 160, and the cover 115 may be coupled to the rear case 114 in an integrated structure. The integrated structure of the wireless charging module 150, the optical sensor module 160, and the cover 115 will be described below in more detail with reference to FIG. 8.

In an embodiment, the display 120 may be disposed between the front plate 111 and the bracket 130. The display 120 may be visually exposed through the front plate 111 in a direction (e.g., the first direction D1) toward the front side of the housing 110. For example, the display 120 may be attached to the front plate 111. The display 120 may be electrically connected to the circuit board 140. For example, one surface of the display 120 may be disposed to face one surface of the circuit board 140 with the bracket 130 therebetween, and a connector (not illustrated) of the display 120 may be connected to the circuit board 140 through an opening area (not illustrated) that is formed in the bracket 130.

In an embodiment, the bracket 130 may be disposed in the housing 110 and may support other components (e.g., a support plate 187, the circuit board 140, the contact member 186, and/or the battery 185) of the electronic device 100. The bracket 130 may be assembled to the side frame 112 in the first direction D1. The bracket 130 may be surrounded by the side frame 112. For example, the bracket 130 may be connected to the side frame 112, or may be integrally formed with the side frame 112. The bracket 130 may be formed of a metallic material and/or a nonmetallic (e.g., polymer) material.

In an embodiment, the bracket 130 may be disposed between the circuit board 140 and the display 120. The bracket 130 may provide a battery receiving space 131 in which the battery 185 is accommodated. For example, the circuit board 140 may be disposed on one surface (e.g., the surface facing the second direction D2) of the bracket 130, and the support plate 187 may be disposed on an opposite surface (e.g., the surface facing the first direction D1) of the bracket 130. One surface of the support plate 187 may be disposed to face one surface of the display 120, and the battery 185 may be located between the circuit board 140 and the support plate 187 and may be stably fixed to the bracket 130 accordingly.

In an embodiment, the circuit board 140 may be seated on the bracket 130. For example, the circuit board 140 may be disposed between the back plate 113 and the bracket 130. The circuit board 140 may be disposed to face the back plate 113 and may be disposed to face the display 120 with the bracket 130 therebetween. For example, the circuit board 140 may be located on one surface (e.g., the surface facing the second direction D2) of the bracket 130 and may be disposed in the housing 110 in the state of being spaced apart from the display 120 in the second direction D2.

Figure 13:
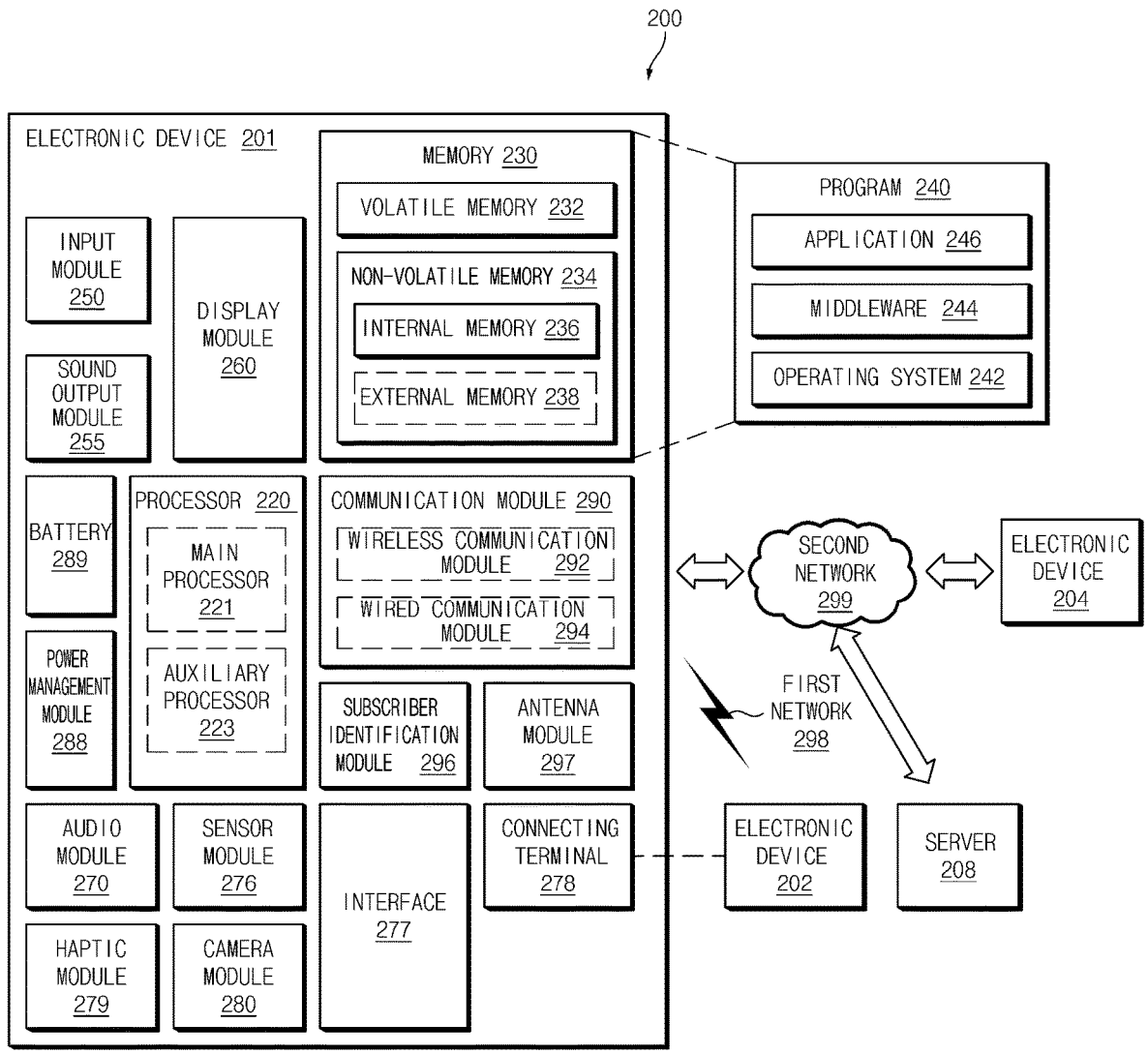
FIG. 13 is a block diagram of an electronic device in a network environment according to certain embodiments.

In an embodiment, the circuit board 140 may have an electronic part located thereon, such as a processor (e.g., a processor 220 of FIG. 13), a memory (e.g., a memory 230 of FIG. 13), a communication module (e.g., a communication module 290 of FIG. 13), various types of sensor modules (e.g., a sensor module 276 of FIG. 13), an interface (e.g., an interface 277 of FIG. 13), or a connecting terminal (e.g., a connecting terminal 278 of FIG. 13). The processor may include, for example, one or more of a central processing unit, an application processor, a graphic processing unit (GPU), a sensor processor, or a communication processor. The memory may include, for example, a volatile memory or a nonvolatile memory. The interface may include, for example, a high definition multimedia interface (HDMI), a universal serial bus (USB) interface, an SD card interface, or an audio interface. The interface may electrically or physically connect the electronic device 100 with an external electronic device and may include a USB connector, an SD connector, an MMC connector, or an audio connector.

In an embodiment, the wheel member 181 may be disposed on the front surface of the housing 110. The wheel member 181 may be disposed on the side frame 112 to surround the periphery of the front plate 111. The wheel member 181 may be coupled to the side frame 112 so as to be rotatable. For example, the wheel member 181 may be formed in a circular shape to correspond to the shape of the front plate 111 and/or the side frame 112. However, the shape of the wheel member 181 is not limited to the illustrated embodiment. In certain embodiments, the electronic device 100 may sense and/or detect a rotary motion of the wheel member 181 and may execute various functions of the electronic device 100. For example, the electronic device 100 may be configured to change a screen displayed on the display 120 or adjust volume in a multimedia playback mode in response to rotation of the wheel member 181.

In an embodiment, the button members 182 and 183 may be disposed on the side surface of the housing 110. For example, the button members 182 and 183 may be used as input units for user inputs. In an embodiment, the button members 182 and 183 may include the first button member 182 and/or the second button member 183. However, the number of button members 182 and 183 is not limited to the illustrated embodiment, and according to certain embodiments, the electronic device 100 may not include one of the button members 182 and 183, or may additionally include another button member (e.g., a third button member (not illustrated)).

In an embodiment, at least one of the button members 182 and 183 may be used as an electrode for detecting a biometric signal of the user. For example, the first button member 182 may be used as an electrode button for detecting a biometric signal of the user. The first button member 182 may include an electrode member 182a. The electrode member 182a may be configured to be electrically connected with the circuit board 140 through the contact member 186.

In an embodiment, at least part of the electrode member 182a may be exposed on the side surface of the housing 110 so as to make contact with a part (e.g., a finger) of the user's body. At least part of the electrode member 182a may be formed of a conductive material. The electrode member 182a may be configured to receive an electrical signal from the user's body and transfer the received electrical signal to control circuitry (e.g., the processor 220 of FIG. 13) disposed on the circuit board 140.

In an embodiment, the user's biometric signal detected through the first button member 182 may be a signal related to an electrocardiogram. For example, when the first button member 182 (the electrode member 182a), the first electrode area (e.g., the first electrode area 119a of FIG. 2), and the second electrode area (e.g., the second electrode area 119b of FIG. 2) make contact with the user's body, a flow of an electrical signal may be formed between the first button member 182 and the first electrode area 119a or between the first button member 182 and the second electrode area 119b, and the electronic device 100 may detect a biometric signal related to an electrocardiogram from the flow of the electrical signal.

In certain embodiments, the second biosensor module (e.g., the second biosensor module 119a and 119b of FIG. 2) of the electronic device 100 may be an electrocardiogram sensor module for measurement of an electrocardiogram, and the second biosensor module may be formed of the first button member 182, the first electrode area 119a, and the second electrode area 119b.

In an embodiment, the first button member 182 may be configured to press a switch 186a depending on a push operation by the user. The first button member 182 may operate the switch 186a by moving in a direction (e.g., a third direction D3) toward the switch 186a depending on the push operation of the user. For example, the first button member 182 may press the switch 186a of the contact member 186 depending on the push operation in the state of being brought into contact with a portion of the contact member 186. Although not illustrated, in certain embodiments, likewise to the first button member 182, the second button member 183 may be configured to press another switch (not illustrated) depending on a user operation.

In an embodiment, the sealing member 184 may be disposed between the back plate 113 and the side frame 112. For example, the sealing member 184 may seal the area where the rear case 114 of the back plate 113 and the side frame 112 make contact with each other in the state in which the back plate 113 and the side frame 112 are assembled. The sealing member 184 may block infiltration of foreign matter and/or moisture from outside the housing 110 through a space between the rear case 114 and the side frame 112.

In an embodiment, the battery 185 may supply power to at least some of the components of the electronic device 100. For example, the battery 185 may include a primary cell that is not rechargeable, a secondary cell that is rechargeable, or a fuel cell. The battery 185 may be supported by the bracket 130 and may be disposed in the housing 110 accordingly. For example, at least part of the battery 185 may be surrounded by the bracket 130. In certain embodiments, the battery 185 may be integrally disposed inside the electronic device 100, or may be disposed to be detachable from the electronic device 100.

Although not illustrated in FIGS. 3 and 4, the electronic device 100 may further include an antenna (not illustrated) (e.g., an antenna module 297 of FIG. 13) provided in the form of a flat plate or a thin film. In certain embodiments, the antenna may be disposed between the display 120 and the bracket 130, or may be disposed between the circuit board 140 and the back plate 113. The antenna may perform short-range communication with an external device, or may wirelessly transmit and receive power utilized for charging, and may transmit a magnetism-based signal including a short-range communication signal or payment data. For example, the antenna may include at least one of a near field communication (NFC) antenna, a wireless charging antenna, or a magnetic secure transmission (MST) antenna. In certain embodiments, the electronic device 100 may be configured such that at least part of the housing 110 functions as an antenna. For example, an antenna structure may be formed by a portion of the side frame 112 and/or a portion of the bracket 130, or a combination thereof.

Figure 5:
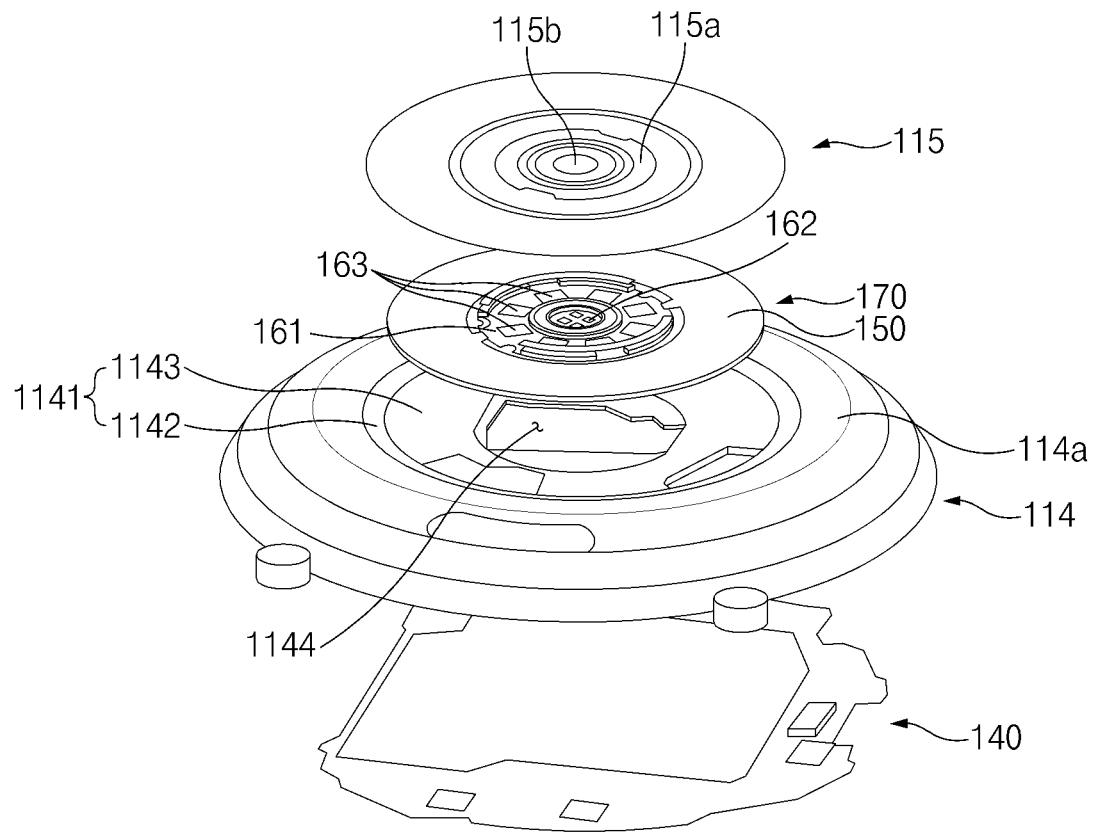
FIG. 5 illustrates a back plate, a circuit board, and a module assembly of the electronic device according to an embodiment.
Figure 6:
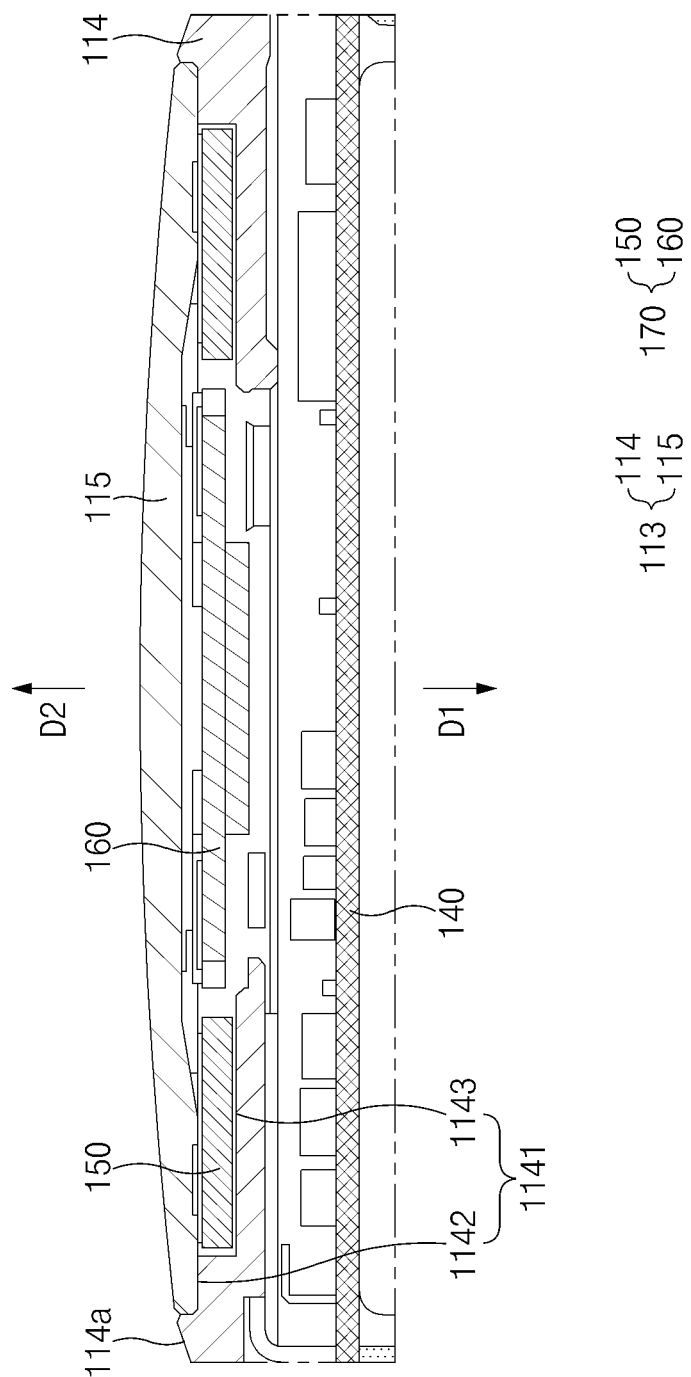
FIG. 6 illustrates the back plate, the circuit board, and the module assembly of the electronic device according to an embodiment.

FIG. 5 illustrates the back plate, the circuit board, and a module assembly of the electronic device according to an embodiment. FIG. 6 illustrates the back plate, the circuit board, and the module assembly of the electronic device according to an embodiment.

FIG. 5 is a perspective view illustrating the state in which the back plate 113, the circuit board 140, and the module assembly 170 are disassembled. FIG. 6 is a sectional view illustrating the state in which the back plate 113, the circuit board 140, and the module assembly 170 are coupled or assembled.

Referring to FIGS. 5 and 6, the electronic device 100 according to an embodiment may include the back plate 113, the circuit board 140, and the module assembly 170. Components of the electronic device 100 illustrated in FIGS. 5 and 6 may be identical or similar to some of the components of the electronic device 100 illustrated in FIGS. 1 to 4, and repetitive descriptions will hereinafter be omitted.

In an embodiment, the back plate 113 may include the rear case 114 and the cover 115. For example, the back plate 113 may be formed by a coupling of the rear case 114 and the cover 115. In certain embodiments, the cover 115 may be attached to at least a partial area of the rear case 114.

In an embodiment, the rear case 114 may include a first surface 114a that forms the rear surface of the electronic device 100 and a second surface (not illustrated) that faces away from the first surface 114a. The first surface 114a may face the second direction D2, and the second surface may face the first direction D1. For example, at least part of the first surface 114a may face the cover 115 and the module assembly 170, and at least part of the second surface may face the circuit board 140.

In an embodiment, the rear case 114 may include a seating portion 1141 on which the cover 115 and the module assembly 170 are disposed. The seating portion 1141 may be formed on at least part of the first surface 114a of the rear case 114. For example, at least part of the first surface 114a may be recessed toward the second surface to form the seating portion 1141. In certain embodiments, the seating portion 1141 may be formed in a shape corresponding to the cover 115.

In an embodiment, the seating portion 1141 may include a first area 1142 connected with the first surface 114a in a stepped manner in the first direction D1, and a second area 1143 connected with the first area 1142 in a stepped manner in the first direction D1. For example, the first area 1142 may refer to an area surrounding the periphery of the second area 1143. The cover 115 may be disposed on the first area 1142, and the module assembly 170 may be disposed on the second area 1143. For example, the cover 115 may be attached to at least part of the first area 1142, and the module assembly 170 may be attached to at least part of the second area 1143.

In certain embodiments, the module assembly 170 may not be attached to the rear case 114. For example, the module assembly 170 may be coupled or attached with the cover 115 to form an integrated part and may be fixedly disposed between the second area 1143 and the cover 115 as the cover 115 is attached to the first area 1142.

In an embodiment, an opening 1144 may be formed in at least a partial area of the seating portion 1141. Although not illustrated, a connecting member (e.g., a connecting member 189 of FIG. 12) connecting the module assembly 170 and the circuit board 140 may be located in the opening 1144. For example, the connecting member 189 may extend through the opening 1144 and may electrically connect the module assembly 170 and the circuit board 140 disposed on opposite sides of the rear case 114 (e.g., refer to FIG. 12). The position and shape of the opening 1144 and/or the number of openings 144 are not limited to the illustrated embodiment.

In an embodiment, the cover 115 may be attached to the module assembly 170 and may be coupled to the rear case 114 in a state in which the module assembly 170 is attached to the cover 115. For example, the cover 115 and the module assembly 170 may be attached to each other, and may be modularized into an integrated part.

In an embodiment, for operation of the optical sensor module 160, at least part of the cover 115 may be formed transparent such that at least some incident light is able to pass through the cover 115. For example, the cover 115 may include transparent areas 115a and 115b formed in positions corresponding to a light emitting part 162 and a light receiving part 163 of the optical sensor module 160. In certain embodiments, light generated from the light emitting part 162 of the optical sensor module 160 may pass through the transparent areas 115a and 115b and may reach an external object (e.g., a wrist of the user), and light reflected from the external object may pass through the transparent areas 115a and 115b and may reach the light receiving part 163.

In an embodiment, the module assembly 170 may be disposed between the cover 115 and the rear case 114. For example, the module assembly 170 may be accommodated in a space between the cover 115 and the seating portion 1141. According to an embodiment, the module assembly 170 may be coupled or attached to the cover 115. The module assembly 170, together with the cover 115, may be provided as an integrated part, and may be integrally assembled to the rear case 114. An operation of assembling the module assembly 170, the cover 115, and the rear case 114 will be described below in more detail with reference to FIG. 12.

In an embodiment, the module assembly 170 may be configured such that a component for wirelessly charging the battery (e.g., the battery 185 of FIG. 4) and a component for sensing a biometric signal of the user are integrally formed with each other. For example, the module assembly 170 may include the wireless charging module 150 and the optical sensor module 160. The wireless charging module 150 and the optical sensor module 160 may be partially connected or coupled so as to be integrated with each other.

In an embodiment, the module assembly 170 may be electrically connected with the circuit board 140. For example, the module assembly 170 may be include a form in which the wireless charging module 150 and the optical sensor module 160 are electrically and physically connected, and may both be electrically connected to the circuit board 140 through the connecting member (e.g., the connecting member 189 of FIG. 12), which itself may be connected to at least one of the wireless charging module 150 or the optical sensor module 160. In an embodiment, the wireless charging module 150 and the optical sensor module 160 may be integrally formed with each other and may be connected with the circuit board 140 through the one connecting member 189 (e.g., refer to FIG. 12).

In an embodiment, the wireless charging module 150 may wirelessly receive power from an external electronic device (e.g., a wireless charging device). For example, the wireless charging module 150 may include a wireless charging coil (e.g., an Rx-coil) having a flat plate shape, and may generate a current by electromagnetic induction generated from the external electronic device. The electronic device 100 may thus charge the battery (e.g., the battery 185 of FIG. 4) using the current generated from the wireless charging module 150. In certain embodiments, the wireless charging module 150 may support one or more wireless charging methods including a magnetic resonance method or a magnetic induction method.

In an embodiment, the wireless charging module 150 surround the optical sensor module 160. For example, the wireless charging module 150 may surround a flexible circuit board 161 of the optical sensor module 160. The wireless charging module 150 may be formed in a ring shape such that the optical sensor module 160 is located therein. For example, an opening (e.g., an opening 154 of FIGS. 9 and 10) having a shape corresponding to the flexible circuit board 161 may be formed in a central area of the wireless charging module 150. At least part of the wireless charging module 150 may extend toward the optical sensor module 160 so as to be physically and electrically connected to the optical sensor module 160.

In an embodiment, at least part of the optical sensor module 160 may be surrounded by the wireless charging module 150. For example, the optical sensor module 160 may be located within the wireless charging module 150 so as to face a central area of the cover 115. The optical sensor module 160 may be disposed such that at least part thereof faces the transparent areas 115a and 115b of the cover 115.

In an embodiment, the optical sensor module 160 (e.g., the first biosensor module 118 of FIG. 2) may detect a biometric signal of the user. For example, the biometric signal detected by the optical sensor module 160 may relate to the user's heart rate. In certain embodiments, the optical sensor module 160 may include a heart rate monitor (HRM) sensor.

In an embodiment, the optical sensor module 160 may include the flexible circuit board 161 (e.g., a flexible printed circuit board or "FPCB"), the light emitting part 162, and the light receiving part 163. The light emitting part 162 and the light receiving part 163 may be disposed on one surface of the flexible circuit board 161. For example, the light emitting part 162 and the light receiving part 163 may be disposed on one surface (e.g., the surface facing the second direction D2) of the flexible circuit board 161 that faces the cover 115. The light emitting part 162 and the light receiving part 163 may be aligned with the transparent areas 115a and 115b of the cover 115.

In an embodiment, the light emitting part 162 may emit light to the outside (e.g., the external environment), and the light receiving part 163 may receive reflected light corresponding to the light emitted from the light emitting part 162. For example, the light emitting part 162 may be disposed on the one surface of the flexible circuit board 161 and may emit light in the second direction D2. The light emitting part 162 may emit light towards an external object (e.g., the user's body) making contact with the back cover 115, and the light receiving part 163 may receive light reflected off the external object back towards the light receiving part 163.

In an embodiment, at least part of the optical sensor module 160 may be physically and electrically connected to the wireless charging module 150 such that the optical sensor module 160 is integrated with the wireless charging module 150. For example, the flexible circuit board 161 of the optical sensor module 160 may be connected or coupled with a portion of the wireless charging module 150.

In an embodiment, the optical sensor module 160 may detect a biometric signal related to a heart rate by measuring the amount of reflected light using an optical sensor. For example, light generated from the light emitting part 162 may reach the user's body through the cover 115, a portion of the light emitted from the light emitting part 162 may be reflected off a blood flow in a blood vessel of the user, and the light receiving part 163 may receive the reflected light. For example, the optical sensor module 160 may be implemented with a photoplethysmography (PPG) sensor.

A coupling structure and components of the module assembly 170 in which the optical sensor module 160 and the wireless charging module 150 are integrally formed with each other will be described below in more detail with reference to FIGS. 7 and 8.

Figure 7:
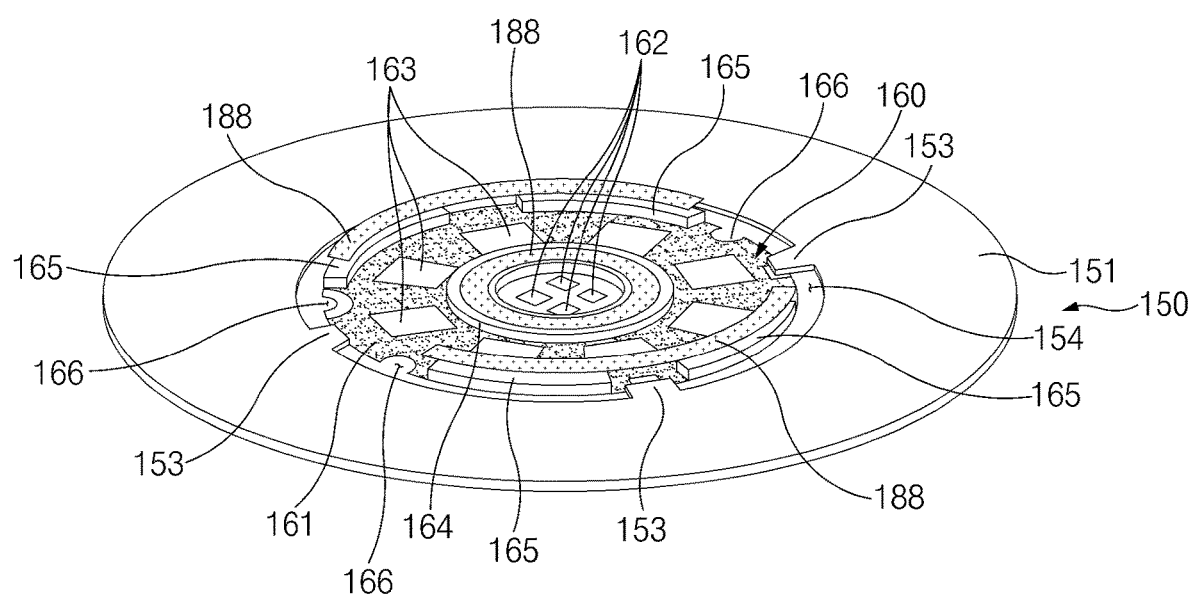
FIG. 7 illustrates the module assembly of the electronic device according to an embodiment.

FIG. 7 illustrates the module assembly of the electronic device according to an embodiment. FIG. 8 illustrates the module assembly and the cover of the electronic device according to an embodiment.

Figure 8:
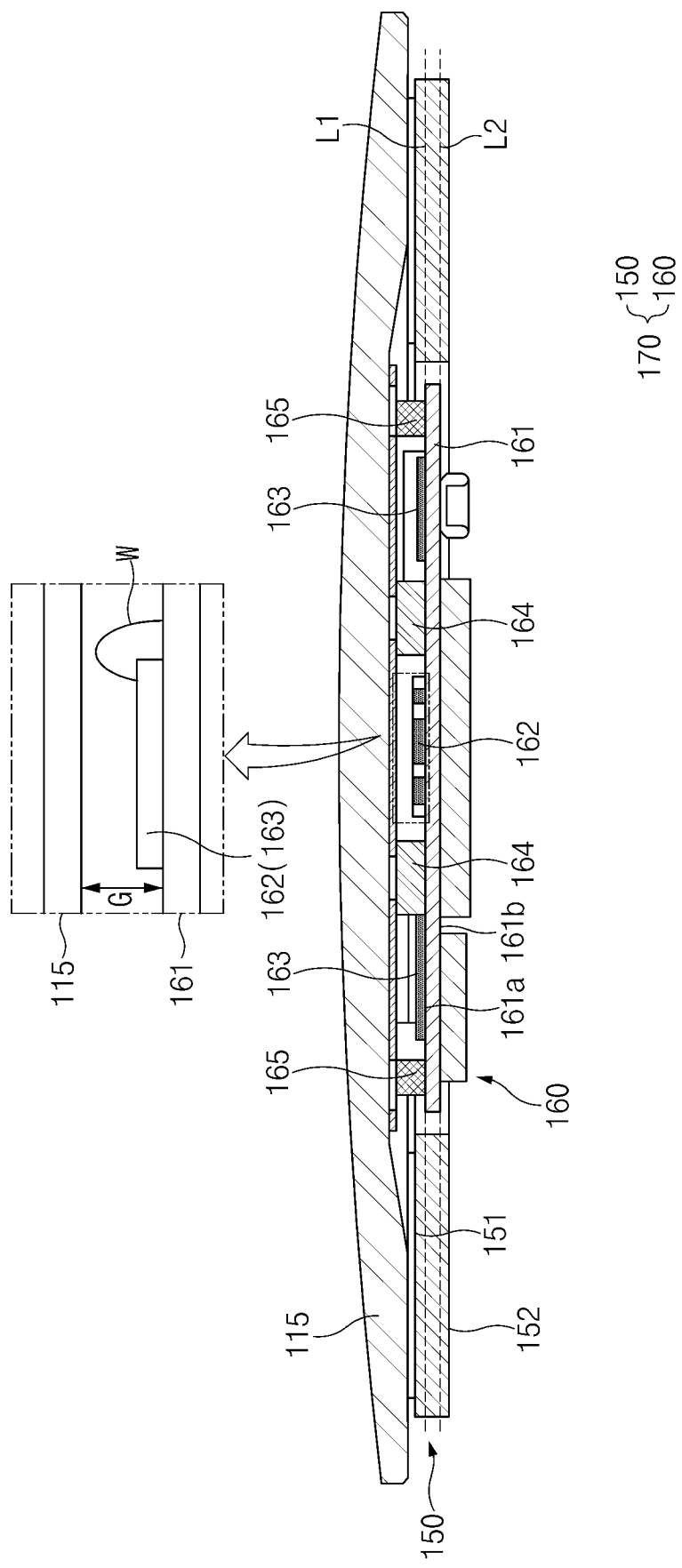
FIG. 8 illustrates the module assembly and a cover of the electronic device according to an embodiment.

Referring to FIGS. 7 and 8, the electronic device 100 according to an embodiment may include the module assembly 170 and the cover 115. The module assembly 170 and the cover 115 may be attached to each other through an adhesive member 188.

In an embodiment, the module assembly 170 may include the wireless charging module 150 and the optical sensor module 160 integrally formed with each other. For example, the wireless charging module 150 and the optical sensor module 160 may be integrally formed with each other by connection of at least some portions of each module.

In an embodiment, the wireless charging module 150 may include at least one connecting portion 153 that is connected to the optical sensor module 160. For example, the wireless charging module 150 may have, in a central area thereof, an opening 154 in which the optical sensor module 160 is located. The connecting portion 153 may extend from the periphery of the opening 154 towards the optical sensor module 160.

In an embodiment, the connecting portion 153 may be connected with the flexible circuit board 161 of the optical sensor module 160, and the wireless charging module 150 may be integrally formed with the optical sensor module 160 accordingly. For example, the connecting portion 153 may be coupled to at least part of the flexible circuit board 161. In certain embodiments, the connecting portion 153 may be coupled with the flexible circuit board 161 through a laser soldering process. However, a method of coupling the connecting portion 153 and the flexible circuit board 161 is not limited to the above-described example, and the connecting portion 153 may be coupled with the flexible circuit board 161 by using various coupling methods.

In an embodiment, the wireless charging module 150 may be physically and electrically connected with the optical sensor module 160 through the connecting portion 153. For example, the connecting portion 153 may include a conductive area (not illustrated) so as to be electrically connected with the flexible circuit board 161. The connecting portion 153 and the flexible circuit board 161 may include conductive areas (not illustrated) that correspond to each other, and the connecting portion 153 and the flexible circuit board 161 may be coupled such that the respective conductive areas of each module contact each other. Accordingly, the connecting portion 153 may be physically and electrically connected with the flexible circuit board 161.

In an embodiment, the wireless charging module 150 may include a third surface 151 facing the cover 115 and a fourth surface 152 facing away from the third surface 151. At least part of the third surface 151 of the wireless charging module 150 may be attached to the cover 115.

In an embodiment, the optical sensor module 160 may include the flexible circuit board 161, the light emitting part 162, the light receiving part 163, a first sidewall 164, and/or a second sidewall 165.

In an embodiment, the flexible circuit board 161 may include a first surface 161a facing the cover 115 and a second surface 161b facing away from the first surface 161a. The light emitting part 162, the light receiving part 163, the first sidewall 164, and/or the second sidewall 165 may be disposed on the first surface 161a of the flexible circuit board 161. For example, the light emitting part 162, the light receiving part 163, the first sidewall 164, and/or the second sidewall 165 may be located between the first surface 161a of the flexible circuit board 161 and the cover 115. Various electrical elements (e.g., an electrical element 168 of FIG. 10) and/or various connectors (e.g., a connector 167 of FIG. 10) may be disposed on the second surface 161b of the flexible circuit board 161.

In an embodiment, the flexible circuit board 161 may be coupled with the connecting portion 153 of the wireless charging module 150. For example, the connecting portion 153 may be disposed on an edge area of the first surface 161a of the flexible circuit board 161, and the flexible circuit board 161 may be coupled with the connecting portion 153 through various coupling methods (e.g., laser soldering).

The flexible circuit board 161 may be electrically connected with the wireless charging module 150 through the connecting portion 153.

In an embodiment, the flexible circuit board 161 may be located on substantially the same plane as the wireless charging module 150. For example, when a section of the module assembly 170 is viewed, the flexible circuit board 161 may be located between the third surface 151 and the fourth surface 152 of the wireless charging module 150. In certain embodiments, the first surface 161a of the flexible circuit board 161 may form the same plane as the third surface 151 or may be located between the third surface 151 and the fourth surface 152, and the second surface 161b may form the same plane as the fourth surface 152 or may be located between the third surface 151 and the fourth surface 152.

For example, as illustrated in FIG. 8, two virtual lines may be defined, including a first virtual extension line L1 extending parallel to the first surface 161a from the first surface 161a of the flexible circuit board 161 and a second virtual extension line L2 extending parallel to the second surface 161b from the second surface 161b, and the first extension line L1 and the second extension line L2 may be located between the third surface 151 and the fourth surface 152 of the wireless charging module 150. According to an embodiment, as the flexible circuit board 161 and the wireless charging module 150 are aligned so as not to have a step in the height-wise direction (e.g., the "thickness" direction, or first direction D1 and the second direction D2) of the electronic device 100, the flexible circuit board 161 and the wireless charging module 150 may be more easily connected through the connecting portion 153.

In an embodiment, at least one hole 166 may be formed at the edge of the flexible circuit board 161. The hole 166 may penetrate the first surface 161a and the second surface 161b of the flexible circuit board 161. For example, at least part of the edge of the flexible circuit board 161 may be concavely recessed to form the hole 166 in a form in which one side is open. For example, a plurality of holes 166 may be formed. The plurality of holes 166 may be spaced apart from each other along the edge of the flexible circuit board 161. According to the illustrated embodiment, the hole 166 may be connected with the edge of the flexible circuit board 161 and may be formed in an open form. However, the shape of the hole 166 is not limited thereto. For example, the hole 166 may be formed in a closed form (e.g., the form of a closed curve) without being connected with the edge of the flexible circuit board 161.

Figure 10:
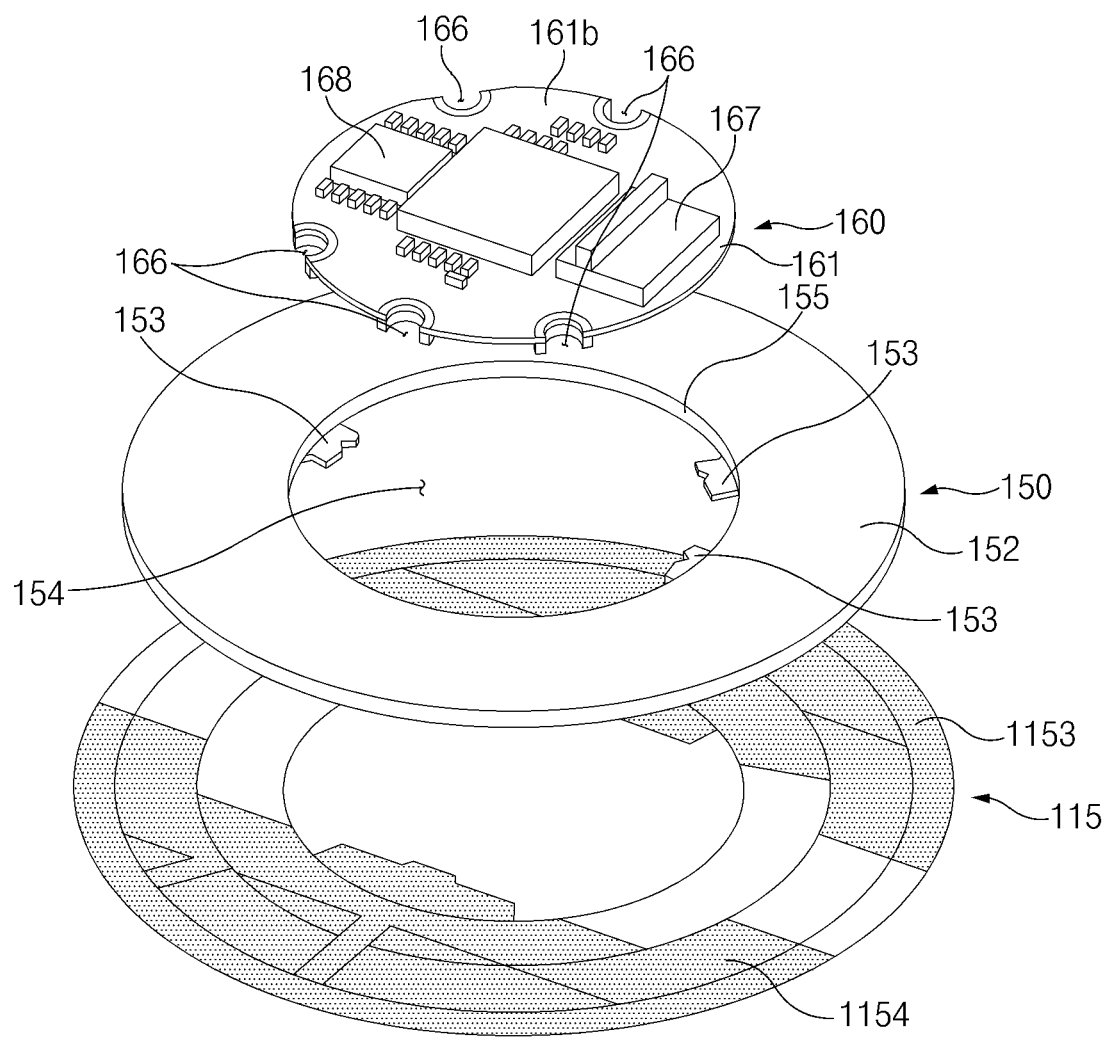
FIG. 10 illustrates the cover, the wireless charging module, and the optical sensor module of the electronic device according to an embodiment.
Figure 11:
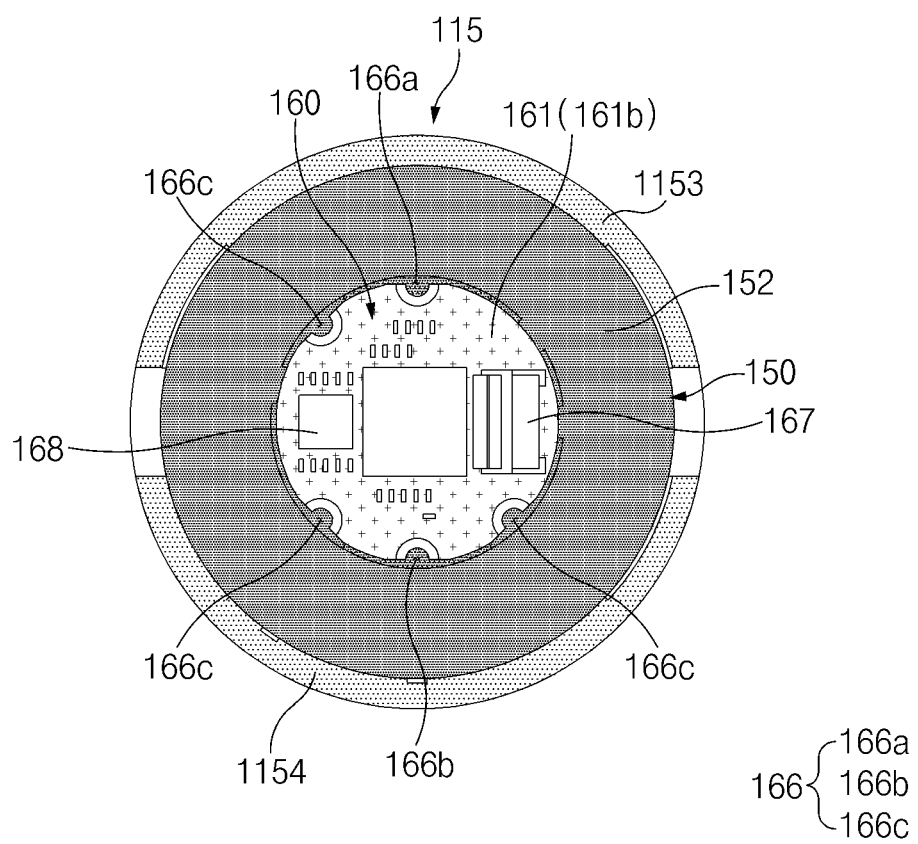
FIG. 11 illustrates the cover, the wireless charging module, and the optical sensor module of the electronic device according to an embodiment.

In certain embodiments, the hole 166 may be filled with a conductive material (not illustrated), and an electrical path may be formed between electrodes (e.g., electrodes 1151, 1152, 1153, and 1154 of FIGS. 9 to 11) on the cover 115 and electrical elements (e.g., the electrical element 168 of FIGS. 10 and 11) on the second surface 161b of the circuit board 140 through the conductive material (e.g., refer to FIG. 11).

In an embodiment, the light emitting part 162 may be disposed on the first surface 161a of the flexible circuit board 161. The light emitting part 162 disposed on the first surface 161a may emit light toward the cover 115. For example, the light emitting part 162 may include an LED. In certain embodiments, the light emitting part 162 may emit light having various colors. The light emitted from the light emitting part 162 may have a wavelength range of about 380 nm to about 800 nm. For example, the light emitting part 162 may emit green light, and the green light may have a wavelength range of about 492 nm to about 575 nm.

In an embodiment, the light emitting part 162 may be disposed on the central area of the first surface 161a of the flexible circuit board 161. The light emitting part 162 may include one or more light emitting elements. The light emitting part 162 may be located inward of the first sidewall 164 and may be spaced apart from the light receiving part 163. For example, the light emitting part 162 may be configured to be located in a space separated from the light receiving part 163 by the first sidewall 164 formed between the light emitting part 162 and the light receiving part 163.

In an embodiment, the light receiving part 163 may be disposed on the first surface 161a of the flexible circuit board 161. The light receiving part 163 may be spaced apart from the light emitting part 162 by a predetermined distance and may be disposed to surround an area around the light emitting part 162. For example, a plurality of light receiving parts 163 may be formed. The plurality of light receiving parts 163 may be disposed in a radial direction along the periphery of the light emitting part 162 or the first sidewall 164. For example, the plurality of light receiving parts 163 may be arranged along the outer circumferential surface of the first sidewall 164. Although eight light receiving parts 163 are illustrated in FIG. 7, the number of light receiving parts 163 and the positions thereof may be diversely changed without being limited to the illustrated embodiment. The light receiving part 163 may receive light reflected off an external object. For example, the light receiving part 163 may include a photo diode (PD).

In an embodiment, the light emitting part 162 and the light receiving part 163 may be electrically connected with the flexible circuit board 161. For example, the light emitting part 162 and the light receiving part 163 may be disposed on the first surface 161a so as to be electrically connected with the flexible circuit board 161. In certain embodiments, the light emitting part 162 and the light receiving part 163 may be disposed on the flexible circuit board 161 in a chip on board (COB) manner. For example, elements (e.g., LED chips and/or PD chips) of the light emitting part 162 and the light receiving part 163 may be directly attached to the first surface 161a of the flexible circuit board 161 by using an adhesive member (e.g., Ag epoxy) formed of a conductive material and may be wire-bonded to the flexible circuit board 161 by using wires "W." Accordingly, the thickness of the optical sensor module 160 may be reduced.

In certain embodiments, as the light emitting part 162 and the light receiving part 163 are disposed in a COB manner, the plurality of elements and wires W exposed on the flexible circuit board 161 may be protected by the sidewalls (e.g., the first sidewall 164 and the second sidewall 165) and the cover 115.

In an embodiment, the first sidewall 164 may be disposed on the first surface 161a of the flexible circuit board 161 to surround the light emitting part 162. For example, the first sidewall 164 may be formed in a hollow form such that the light emitting part 162 is located within the hollow cavity. Although FIG. 7 illustrates an example that the first sidewall 164 is formed in a hollow cylindrical shape, this is illustrative, and the first sidewall 164 may be formed in various shapes including a hollow polygonal shape.

In an embodiment, the first sidewall 164 may be located between the light emitting part 162 and the light receiving part 163. For example, when the first surface 161a of the flexible circuit board 161 is viewed from above, the first sidewall 164 may be formed between the light emitting part 162 and the light receiving part 163 to surround the light emitting part 162. In certain embodiments, the light emitting part 162 and the light receiving part 163 may be separated from each other by the first sidewall 164. The first sidewall 164 may function as a partition wall between the light emitting part 162 and the light receiving part 163. As illustrated in FIG. 8, the first sidewall 164 may block the space between the light emitting part 162 and the light receiving part 163 such that the light emitting part 162 and the light receiving part 163 are separated from each other. For example, the first sidewall 164 may block a path along which light emitted from the light emitting part 162 directly moves to the light receiving part 163 without travelling outside the electronic device 100 through the cover 115, thereby preventing the light receiving part 163 from receiving coherent light other than reflected light.

In an embodiment, the first sidewall 164 may include a magnetic material. For example, the first sidewall 164 may be formed of a magnet. When the first sidewall 164 is formed of a magnet, the first sidewall 164 may interact with a magnet included in an external electronic device (e.g., a wireless charging device) to stably mount the electronic device 100 on the charging device, and may align an antenna included in the wireless charging device and the wireless charging module 150 to allow the electronic device 100 to be located in a position in which charging is performable.

In an embodiment, the first sidewall 164 may be attached to the back cover 115. For example, the first sidewall 164 may be coupled with the back cover 115 through at least one adhesive member 188 disposed between the first sidewall 164 and the back cover 115. The first sidewall 164 may protrude out to a predetermined height from the first surface 161a of the flexible circuit board 161, and the cover 115 and the flexible circuit board 161 may be spaced apart from each other at a predetermined interval "G" by the first sidewall 164. For example, the first sidewall 164 may prevent collision and/or interference of the cover 115 with the light emitting part 162 or the light receiving part 163 by spacing the cover 115 apart from the first surface 161a of the flexible circuit board 161 by the predetermined interval G. In certain embodiments, the predetermined interval G may range from about 0.4 mm to about 0.6 mm and may be 0.5 mm.

In an embodiment, the second sidewall 165 may be disposed along an edge portion of the flexible circuit board 161. For example, the second sidewall 165 may be located adjacent to an edge portion of the first surface 161a of the flexible circuit board 161. The second sidewall 165 may be spaced apart from the first sidewall 164 at a predetermined interval, and the light receiving part 163 may be located between the first sidewall 164 and the second sidewall 165. For example, the second sidewall 165 may surround at least a portion of the light receiving part 163. A plurality of second sidewalls 165 may be formed. The plurality of second sidewalls 165 may be spaced apart from each other along the edge of the first surface 161a.

In an embodiment, the second sidewall 165 may have substantially the same height as the first sidewall 164. For example, the second sidewall 165, together with the first sidewall 164, may provide a function of protecting the light emitting part 162 and the light receiving part 163 such that the light emitting part 162 and the light receiving part 163 do not collide with the cover 115. The second sidewall 165 may be attached to the back cover 115. For example, the second sidewall 165 may be coupled with the back cover 115 through at least one adhesive member 188 disposed between the second sidewall 165 and the back cover 115. The second sidewall 165 may protrude to a predetermined height from the first surface 161a of the flexible circuit board 161, and the cover 115 and the flexible circuit board 161 may be spaced apart from each other at the predetermined interval G by the second sidewall 165. For example, the second sidewall 165 may prevent collision and/or interference of the cover 115 with the light emitting part 162 or the light receiving part 163 by spacing the cover 115 apart from the first surface 161a of the flexible circuit board 161 at the predetermined interval G.

According to the embodiment illustrated in FIG. 7, the second sidewall 165 may be formed in a circular shape, the center of which is located on the flexible circuit board 161, so as to surround at least a portion of the light receiving part 163. However, the shape of the second sidewall 165 is not limited thereto. The second sidewall 165 may protect the light receiving part 163 and the light emitting part 162 by spacing the cover 115 apart from the flexible circuit board 161 at the predetermined interval together with the first sidewall 164, and may be modified in various shapes within a range to provide such a function. For example, the second sidewall 165 may be formed surrounding the hole 166 formed in the flexible circuit board 161. An embodiment in which the shape of the second sidewall 165 is changed will be described below with reference to FIGS. 9 and 10.

According to an embodiment of the disclosure, the module assembly 170 may be configured such that the wireless charging module 150 and the optical sensor module 160 are integrated with each other. For example, the flexible circuit board 161 and the wireless charging module 150 may be aligned on substantially the same plane to couple the connecting portion 153 of the wireless charging module 150 to the flexible circuit board 161 of the optical sensor module 160. For example, the light emitting part 162 and the light receiving part 163 of the optical sensor module 160 may be disposed on the flexible circuit board 161 in a COB manner, and thus the flexible circuit board 161 may be aligned with the wireless charging module 150 on the same plane. Accordingly, the distance between the flexible circuit board 161 and the cover 115 may be decreased. This may lead to a reduction in the thickness of the set of the electronic device 100, an improvement in the optical performance of the optical sensor module 160, and simplification of the assembly process.

Figure 9:
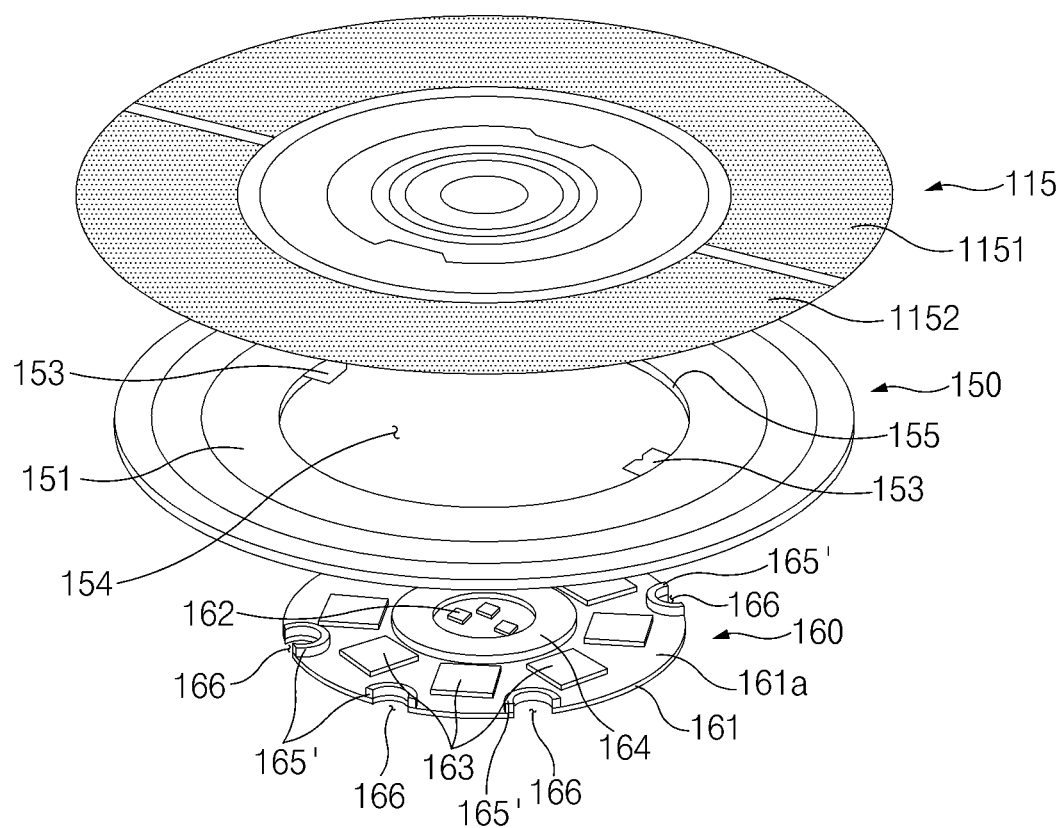
FIG. 9 illustrates the cover, a wireless charging module, and an optical sensor module of the electronic device according to an embodiment.

FIG. 9 illustrates the cover, the wireless charging module, and the optical sensor module of the electronic device according to an embodiment. FIG. 10 illustrates the cover, the wireless charging module, and the optical sensor module of the electronic device according to an embodiment. FIG. 11 illustrates the cover, the wireless charging module, and the optical sensor module of the electronic device according to an embodiment.

FIGS. 9 and 10 may be perspective views illustrating the state in which the cover, the wireless charging module, and the optical sensor module are disassembled. FIG. 11 may be a plan view illustrating the state in which the cover, the wireless charging module, and the optical sensor module are coupled.

Referring to FIGS. 9 to 11, the electronic device 100 according to an embodiment may include the cover 115, the wireless charging module 150, and the optical sensor module 160, and these components may be coupled to form an integrated part.

In an embodiment, the cover 115 may include the plurality of electrodes 1151, 1152, 1153, and 1154 that form the second biosensor module (e.g., the second biosensor module 119a and 119b of FIG. 2). For example, the second biosensor module may include an ECG sensor module for measuring a biometric signal related to the user's electrocardiogram. The plurality of electrodes 1151, 1152, 1153, and 1154 may be formed of a conductive material and may be formed on surfaces of the cover 115. For example, the plurality of electrodes 1151, 1152, 1153, and 1154 may be formed through a method in which the conductive material is deposited on the surfaces of the cover 115.

In an embodiment, the plurality of electrodes 1151, 1152, 1153, and 1154 may include the outside electrodes 1151 and 1152 (e.g., "external" electrodes) exposed to an exterior of the electronic device 100 and the inside electrodes 1153 and 1154 (e.g., "internal" electrodes) located within the electronic device 100. The outside electrodes 1151 and 1152 may be formed on the outside surface (not illustrated) of the cover 115, and the inside electrodes 1153 and 1154 may be formed on the inside surface (not illustrated) of the cover 115. For example, the outside surface of the cover 115 may refer an outer surface of the electronic device 100, or a surface contacting with the user's body (e.g., a user's wrist). The inside surface of the cover 115 may refer to a surface facing the wireless charging module 150 and the optical sensor module 160, and may face away from the outside surface.

In an embodiment, the outside electrodes 1151 and 1152 may include the first electrode 1151 and the second electrode 1152 spaced apart from the first electrode 1151. The inside electrodes 1153 and 1154 may include the third electrode 1153 and the fourth electrode 1154 spaced apart from the third electrode 1153. For example, the first electrode 1151 may be referred to as the first electrode area illustrated in FIG. 2 (e.g., the first electrode area 119a of FIG. 2), and the second electrode 1152 may be referred to as the second electrode area illustrated in FIG. 2 (e.g., the second electrode area 119b of FIG. 2).

In an embodiment, the first electrode 1151 may be electrically connected with the third electrode 1153, and the second electrode 1152 may be electrically connected with the fourth electrode 1154. For example, the first electrode 1151 may extend to the inside surface of the cover 115 to form the third electrode 1153, and the second electrode 1152 may extend to the inside surface of the cover 115 to form the fourth electrode 1154. In certain embodiments, electrical connection of the outside electrodes 1151 and 1152 and the inside electrodes 1153 and 1154 may be implemented through various methods. For example, the outside electrodes 1151 and 1152 and the inside electrodes 1153 and 1154 may be connected through through-holes (not illustrated) that are formed through the cover 115. A conductive material for electrically connecting the inside electrodes 1153 and 1154 and the outside electrodes 1151 and 1152 may be inserted into the through-holes.

In an embodiment, the inside electrodes 1153 and 1154 and the outside electrodes 1151 and 1152 may be electrically connected with the circuit board 140. For example, the inside electrodes 1153 and 1154 and the outside electrodes 1151 and 1152 may be electrically connected with the electrical element 168 (e.g., control circuitry or a processor) disposed on the circuit board 140. The inside electrodes 1153 and 1154 and the outside electrodes 1151 and 1152 may be configured to transmit and/or receive an electrical signal with the electrical element 168. In certain embodiments, the outside electrodes 1151 and 1152 and the inside electrodes 1153 and 1154 may receive an electrical signal from the user's body and may transfer the received electrical signal to the control circuitry (e.g., the processor 220 of FIG. 13) disposed on the circuit board 140.

In an embodiment, the outside electrodes 1151 and 1152 and the inside electrodes 1153 and 1154 may be electrically connected with the flexible circuit board 161 through the conductive material (not illustrated) that is inserted into the hole 166 to pass through the flexible circuit board 161. For example, the inside electrodes 1153 and 1154 may be brought into contact with the conductive material inserted into the hole 166, and the conductive material may be electrically connected to the electrical element 168 and/or a contact portion of the flexible circuit board 161.

In an embodiment, the opening 154 may be formed in the central area of the wireless charging module 150. The opening 154 may be aligned with the optical sensor module 160 such that the optical sensor module 160 is located therein. For example, the optical sensor module 160 may face the cover 115 through the opening 154.

In an embodiment, the wireless charging module 150 may include the at least one connecting portion 153 formed on an inner peripheral portion 155 surrounding the opening 154. The connecting portion 153 may protrude from at least part of the inner peripheral portion 155 toward the center of the opening 154. The connecting portion 153 may be coupled to the first surface 161a of the flexible circuit board 161.

In an embodiment, the connecting portion 153 may be formed to have a step with the fourth surface 152 of the wireless charging module 150. For example, the connecting portion 153 may extend while forming substantially the same plane as the third surface 151 of the wireless charging module 150 and forming a step with the fourth surface 152.

In certain embodiments, the connecting portion 153 may partially face the first surface 161a of the flexible circuit board 161, and a conductive area (not illustrated) may be formed on a partial area of the connecting portion 153 that faces the first surface 161a. The connecting portion 153 may be electrically connected with the flexible circuit board 161 through the conductive area.

In an embodiment, the optical sensor module 160 may include the flexible circuit board 161, the light emitting part 162, the light receiving part 163, the first sidewall 164, and/or a second sidewall 165'.

In an embodiment, the light emitting part 162, the light receiving part 163, the first sidewall 164, and/or the second sidewall 165' may be disposed on the first surface 161a of the flexible circuit board 161, and the electrical element 168 and the connector 167 may be disposed on the second surface 161b facing away from the first surface 161a.

In an embodiment, the flexible circuit board 161 may be electrically connected with the circuit board 140 through the connecting member (e.g., the connecting member 189 of FIG. 12) that connects the connector 167 and the circuit board (e.g., the circuit board 140 of FIGS. 3 and 4). In certain embodiments, the flexible circuit board 161 may be electrically connected with the wireless charging module 150 through the connecting portion 153, and the wireless charging module 150 may be electrically connected with the circuit board 140 through the connecting member 189 connected with the connector 167 of the flexible circuit board 161. According to an embodiment, the wireless charging module 150 and the optical sensor module 160 may be integrally formed with each other and may be electrically connected with the circuit board 140 through one connecting member 189.

In an embodiment, the second sidewall 165' may be formed to surround the hole 166 of the flexible circuit board 161. For example, the second sidewall 165' illustrated in FIG. 9 may be formed in a different structure from the second sidewall illustrated in FIG. 7 (e.g., the second sidewall 165 of FIG. 7). The second sidewall 165' may protrude to a predetermined height from the first surface 161a of the flexible circuit board 161. In certain embodiments, the second sidewall 165' may have substantially the same height as the height by which the first sidewall 164 protrudes.

Hereinafter, an operation in which the cover 115, the wireless charging module 150, and the optical sensor module 160 are manufactured as an integrated part will be described with reference to FIGS. 9 and 10.

In an embodiment, the optical sensor module 160 may be disposed in the opening 154 of the wireless charging module 150 such that the first surface 161a of the flexible circuit board 161 and the connecting portion 153 of the wireless charging module 150 make contact with each other.

In an embodiment, the connecting portion 153 may be coupled to the first surface 161a of the flexible circuit board 161. For example, the connecting portion 153 may be coupled with the flexible circuit board 161 through a laser soldering process, and thus the wireless charging module 150 and the optical sensor module 160 may be physically/electrically connected to be integrated with each other. However, a coupling method of the connecting portion 153 and the flexible circuit board 161 is not limited to the above-described example.

In an embodiment, the wireless charging module 150 and the optical sensor module 160 may be coupled with the cover 115 in the state of being integrally connected with each other. For example, the cover 115 may be attached with the wireless charging module 150 and the optical sensor module 160 through an adhesive member (e.g., a double-sided tape). At least one adhesive member 188 may be disposed between the third surface 151 of the wireless charging module 150 and the cover 115, between the first sidewall 164 and the cover 115, and/or between the second sidewall 165' and the cover 115.

In an embodiment, as the wireless charging module 150 and the optical sensor module 160 are attached with the cover 115, the cover 115, the wireless charging module 150, and the optical sensor module 160 may be manufactured and provided as an integrally modularized part.

Hereinafter, a structure in which the inside electrodes 1153 and 1154 and the outside electrodes 1151 and 1152 are electrically connected with the circuit board 140 through the hole 166 will be described with reference to FIG. 11.

FIG. 11 may be a plan view of the integrated part in which the cover 115, the wireless charging module 150, and the optical sensor module 160 are coupled, and may also illustrate the second surface 161b of the flexible circuit board 161 or the fourth surface of the wireless charging module 150 when viewed from above.

In an embodiment, the cover 115 may partially overlap the wireless charging module 150 and the optical sensor module 160. As illustrated in FIG. 11, at least part of the cover 115 may be visually exposed through the hole 166 of the flexible circuit board 161 when the second surface 161b of the flexible circuit board 161 is viewed from above.

In an embodiment, a plurality of holes 166 may be formed along the periphery of the flexible circuit board 161. For example, at least parts of the inside electrodes 1153 and 1154 disposed on the cover 115 may overlap some of the plurality of holes 166 (e.g., a first hole 166a and a second hole 166b). Furthermore, the remaining area of the cover 115, other than the areas where the inside electrodes 1153 and 1154 are disposed, may overlap the other holes 166 (e.g., third holes 166c).

In an embodiment, a conductive material (not illustrated) may be disposed in some of the plurality of holes 166, and an adhesive material (not illustrated) may be disposed in the other holes. For example, the plurality of holes 166 may include the first hole 166a and the second hole 166b overlapping the inside electrodes 1153 and 1154, and the third holes 166c that are the remaining holes other than the first hole 166a and the second hole 166b. In an embodiment, the first hole 166a and the second hole 166b may be aligned with portions of the inside electrodes 1153 and 1154 in a direction substantially perpendicular to the first surface 161a or the second surface 161b. For example, as illustrated in FIG. 11, the first hole 166a and the second hole 166b may overlap portions of the inside electrodes 1153 and 1154 when the second surface 161b of the flexible circuit board 161 is viewed from above. In certain embodiments, a conductive material may be disposed in the first hole 166a and the second hole 166b, and an adhesive material may be disposed in the third holes 166c.

In an embodiment, the first hole 166a and the second hole 166b may be filled with a conductive material (not illustrated) that makes electrical contact with the inside electrodes 1153 and 1154 formed on the cover 115. For example, the conductive material may be silicone (e.g., Ag silicone) that contains a metallic material. The conductive material disposed in the first hole 166a and the second hole 166b may be electrically connected with the electrical element 168 or the contact portion (not illustrated), which is disposed on the second surface 161b of the flexible circuit board 161, through wires. According to an embodiment, an electrical path may be formed between the inside electrodes 1153 and 1154 (or, the outside electrodes 1151 and 1152) and the circuit board 140 through the conductive material disposed in the first hole 166a and the second hole 166b of the flexible circuit board 161. A method in which the conductive material and the electrical element 168 are electrically connected with each other is not limited to the above-described examples, and may be implemented by using various connecting methods.

In an embodiment, the third holes 166c may be filled with an adhesive material (not illustrated) for fixing the cover 115 and the flexible circuit board 161. For example, the adhesive material may include epoxy. The adhesive material disposed in the third holes 166c may bond the flexible circuit board 161 and the cover 115. Accordingly, the module assembly 170 and the cover 115 may be stably coupled. However, the adhesive material and the third holes 166c may be omitted according to certain embodiments.

Figure 12:
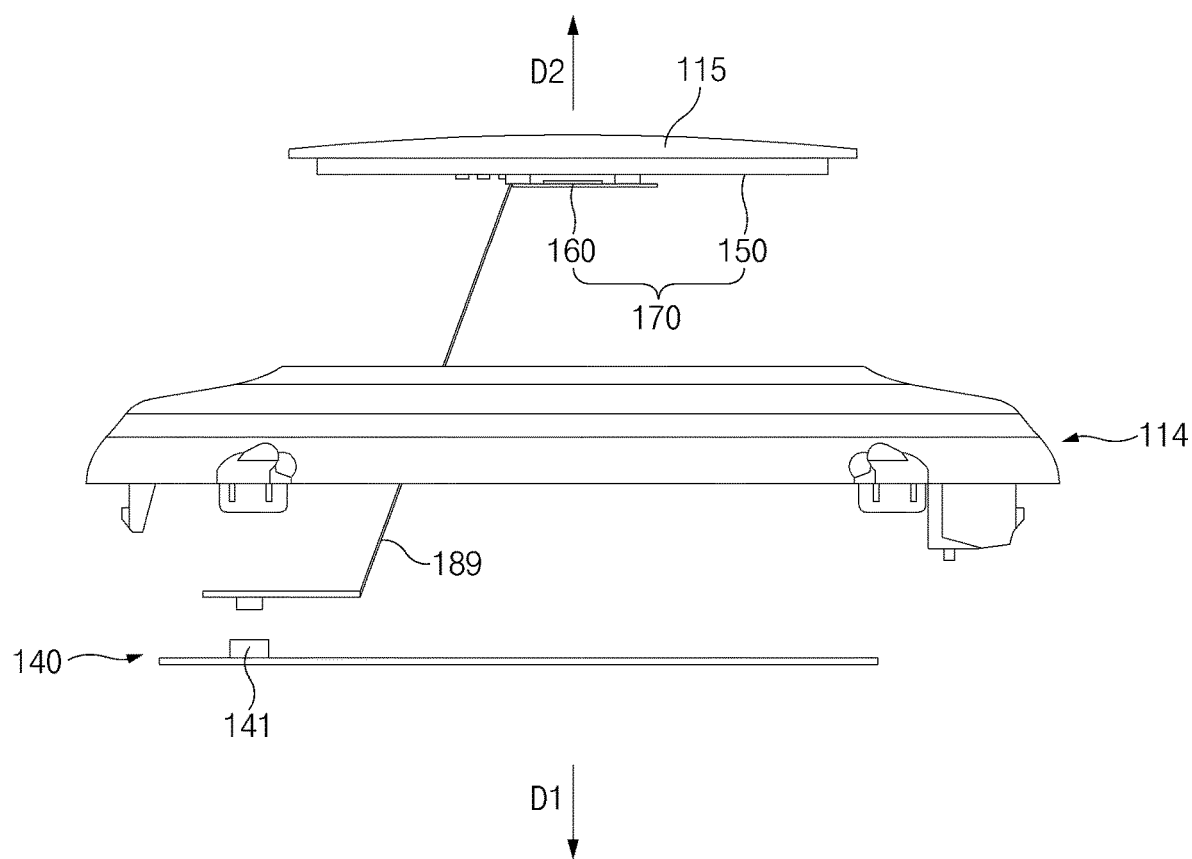
FIG. 12 illustrates an operation in which the module assembly and the cover of the electronic device are coupled with a rear case according to an embodiment.

FIG. 12 illustrates an operation in which the module assembly and the cover of the electronic device are coupled with the rear case according to an embodiment.

FIG. 12 may be a view in which the front plate (e.g., the front plate 111 of FIGS. 3 and 4), the side frame (e.g., the side frame 112 of FIGS. 3 and 4), the display (e.g., the display 120 of FIGS. 3 and 4), and the bracket (e.g., the bracket 130 of FIGS. 3 and 4) of the electronic device 100 are omitted.

Referring to FIG. 12, the module assembly 170 and the cover 115 may be integrally coupled or assembled to the rear case 114.

In an embodiment, the module assembly 170 may be formed in a structure in which the optical sensor module 160 and the wireless charging module 150 are integrally connected with each other, and the module assembly 170 may be coupled with the cover 115. For example, the module assembly 170 and the cover 115 may be provided in the state of being coupled with each other. The module assembly 170 and the cover 115 may be coupled to the rear case 114 in the first direction D1 in the coupled state. In certain embodiments, the module assembly 170 and the cover 115 may be attached to the rear case 114 (e.g., the seating portion 1141 of FIGS. 5 and 6) through an adhesive member (not illustrated).

In an embodiment, the circuit board 140 may be located in the first direction D1 with respect to the rear case 114, and the module assembly 170 and the cover 115 may be located in the second direction D2 with respect to the rear case 114. The module assembly 170 and the circuit board 140 may be disposed on opposite sides of the rear case 114 and may be electrically connected with each other.

In an embodiment, the module assembly 170 may be electrically connected with the circuit board 140 through the connecting member 189. For example, the connecting member 189 may be connected to the optical sensor module 160 (e.g., the connector 167 of the flexible circuit board 161 of FIG. 10) and a connector 141 of the circuit board 140. The connecting member 189 may pass through at least part of the rear case 114. For example, the connecting member 189 may extend from the connector 167 of the optical sensor module 160 toward the connector 141 of the circuit board 140 through an opening (e.g., the opening 1144 of FIG. 5) formed in the rear case 114. The connecting member 189 may include at least one of a flexible printed circuit board (FPCB) or a cable.

In certain embodiments, the electronic device 100 may not include the connecting member 189 and may be configured such that the module assembly 170 is directly connected with the circuit board 140. For example, a connector (e.g., the connector 167 of FIG. 10) of the module assembly 170 and the connector 141 of the circuit board 140 may be aligned in the first direction D1 or the second direction D2 to face each other through the opening 1144 of the rear case 114, and when the module assembly 170 is coupled, the connector of the module assembly 170 and the connector 141 of the circuit board 140 may make direct contact with each other.

According to an embodiment, the module assembly 170 and the cover 115 may be integrally modularized. Accordingly, the assembly process of the electronic device 100 may be simplified, and defects occurring in the assembly process may be reduced. Furthermore, in the electronic device 100, the module assembly 170 (e.g., the wireless charging module 150 and the optical sensor module 160) may be electrically connected to the circuit board 140 by using the one connecting member 189. Accordingly, an arrangement space inside the electronic device 100 may be improved, and manufacturing costs may be reduced.

FIG. 13 is a block diagram illustrating an electronic device 201 in a network environment 200 according to certain embodiments.

Referring to FIG. 13, the electronic device 201 in the network environment 200 may communicate with an electronic device 202 via a first network 298 (e.g., a short-range wireless communication network), or at least one of an electronic device 204 or a server 208 via a second network 299 (e.g., a long-range wireless communication network). According to an embodiment, the electronic device 201 may communicate with the electronic device 204 via the server 208. According to an embodiment, the electronic device 201 may include a processor 220, memory 230, an input module 250, a sound output module 255, a display module 260, an audio module 270, a sensor module 276, an interface 277, a connecting terminal 278, a haptic module 279, a camera module 280, a power management module 288, a battery 289, a communication module 290, a subscriber identification module (SIM) 296, or an antenna module 297. In some embodiments, at least one of the components (e.g., the connecting terminal 278) may be omitted from the electronic device 201, or one or more other components may be added in the electronic device 201. In some embodiments, some of the components (e.g., the sensor module 276, the camera module 280, or the antenna module 297) may be implemented as a single component (e.g., the display module 260).

The processor 220 may execute, for example, software (e.g., a program 240) to control at least one other component (e.g., a hardware or software component) of the electronic device 201 coupled with the processor 220, and may perform various data processing or computation. According to an embodiment, as at least part of the data processing or computation, the processor 220 may store a command or data received from another component (e.g., the sensor module 276 or the communication module 290) in volatile memory 232, process the command or the data stored in the volatile memory 232, and store resulting data in non-volatile memory 234. According to an embodiment, the processor 220 may include a main processor 221 (e.g., a central processing unit (CPU) or an application processor (AP)), or an auxiliary processor 223 (e.g., a graphics processing unit (GPU), a neural processing unit (NPU), an image signal processor (ISP), a sensor hub processor, or a communication processor (CP)) that is operable independently from, or in conjunction with, the main processor 221. For example, when the electronic device 201 includes the main processor 221 and the auxiliary processor 223, the auxiliary processor 223 may be adapted to consume less power than the main processor 221, or to be specific to a specified function. The auxiliary processor 223 may be implemented as separate from, or as part of the main processor 221.

The auxiliary processor 223 may control at least some of functions or states related to at least one component (e.g., the display module 260, the sensor module 276, or the communication module 290) among the components of the electronic device 201, instead of the main processor 221 while the main processor 221 is in an inactive (e.g., sleep) state, or together with the main processor 221 while the main processor 221 is in an active state (e.g., executing an application). According to an embodiment, the auxiliary processor 223 (e.g., an image signal processor or a communication processor) may be implemented as part of another component (e.g., the camera module 280 or the communication module 290) functionally related to the auxiliary processor 223. According to an embodiment, the auxiliary processor 223 (e.g., the neural processing unit) may include a hardware structure specified for artificial intelligence model processing. An artificial intelligence model may be generated by machine learning. Such learning may be performed, e.g., by the electronic device 201 where the artificial intelligence is performed or via a separate server (e.g., the server 208). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 230 may store various data used by at least one component (e.g., the processor 220 or the sensor module 276) of the electronic device 201. The various data may include, for example, software (e.g., the program 240) and input data or output data for a command related thereto. The memory 230 may include the volatile memory 232 or the non-volatile memory 234.

The program 240 may be stored in the memory 230 as software, and may include, for example, an operating system (OS) 242, middleware 244, or an application 246.

The input module 250 may receive a command or data to be used by another component (e.g., the processor 220) of the electronic device 201, from the outside (e.g., a user) of the electronic device 201. The input module 250 may include, for example, a microphone, a mouse, a keyboard, a key (e.g., a button), or a digital pen (e.g., a stylus pen).

The sound output module 255 may output sound signals to the outside of the electronic device 201. The sound output module 255 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 260 may visually provide information to the outside (e.g., a user) of the electronic device 201. The display module 260 may include, for example, a display, a hologram device, or a projector and control circuitry to control a corresponding one of the display, hologram device, and projector. According to an embodiment, the display module 260 may include a touch sensor adapted to detect a touch, or a pressure sensor adapted to measure the intensity of force incurred by the touch.

The audio module 270 may convert a sound into an electrical signal and vice versa. According to an embodiment, the audio module 270 may obtain the sound via the input module 250, or output the sound via the sound output module 255 or a headphone of an external electronic device (e.g., an electronic device 202) directly (e.g., wiredly) or wirelessly coupled with the electronic device 201.

The sensor module 276 may detect an operational state (e.g., power or temperature) of the electronic device 201 or an environmental state (e.g., a state of a user) external to the electronic device 201, and then generate an electrical signal or data value corresponding to the detected state. According to an embodiment, the sensor module 276 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 277 may support one or more specified protocols to be used for the electronic device 201 to be coupled with the external electronic device (e.g., the electronic device 202) directly (e.g., wiredly) or wirelessly. According to an embodiment, the interface 277 may include, for example, a high definition multimedia interface (HDMI), a universal serial bus (USB) interface, a secure digital (SD) card interface, or an audio interface.

A connecting terminal 278 may include a connector via which the electronic device 201 may be physically connected with the external electronic device (e.g., the electronic device 202). According to an embodiment, the connecting terminal 278 may include, for example, a HDMI connector, a USB connector, a SD card connector, or an audio connector (e.g., a headphone connector).

The haptic module 279 may convert an electrical signal into a mechanical stimulus (e.g., a vibration or a movement) or electrical stimulus which may be recognized by a user via his tactile sensation or kinesthetic sensation. According to an embodiment, the haptic module 279 may include, for example, a motor, a piezoelectric element, or an electric stimulator.

The camera module 280 may capture a still image or moving images. According to an embodiment, the camera module 280 may include one or more lenses, image sensors, image signal processors, or flashes.

The power management module 288 may manage power supplied to the electronic device 201. According to an embodiment, the power management module 288 may be implemented as at least part of, for example, a power management integrated circuit (PMIC).

The battery 289 may supply power to at least one component of the electronic device 201. According to an embodiment, the battery 289 may include, for example, a primary cell which is not rechargeable, a secondary cell which is rechargeable, or a fuel cell.

The communication module 290 may support establishing a direct (e.g., wired) communication channel or a wireless communication channel between the electronic device 201 and the external electronic device (e.g., the electronic device 202, the electronic device 204, or the server 208) and performing communication via the established communication channel. The communication module 290 may include one or more communication processors that are operable independently from the processor 220 (e.g., the application processor (AP)) and supports a direct (e.g., wired) communication or a wireless communication. According to an embodiment, the communication module 290 may include a wireless communication module 292 (e.g., a cellular communication module, a short-range wireless communication module, or a global navigation satellite system (GNSS) communication module) or a wired communication module 294 (e.g., a local area network (LAN) communication module or a power line communication (PLC) module). A corresponding one of these communication modules may communicate with the external electronic device via the first network 298 (e.g., a short-range communication network, such as Bluetooth™, wireless-fidelity (Wi-Fi) direct, or infrared data association (IrDA)) or the second network 299 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 292 may identify and authenticate the electronic device 201 in a communication network, such as the first network 298 or the second network 299, using subscriber information (e.g., international mobile subscriber identity (IMSI)) stored in the subscriber identification module 296.

The wireless communication module 292 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 292 may support a high-frequency band (e.g., the mmWave band) to achieve, e.g., a high data transmission rate. The wireless communication module 292 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 292 may support various requirements specified in the electronic device 201, an external electronic device (e.g., the electronic device 204), or a network system (e.g., the second network 299). According to an embodiment, the wireless communication module 292 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 297 may transmit or receive a signal or power to or from the outside (e.g., the external electronic device) of the electronic device 201. According to an embodiment, the antenna module 297 may include an antenna including a radiating element implemented using a conductive material or a conductive pattern formed in or on a substrate (e.g., a printed circuit board (PCB)). According to an embodiment, the antenna module 297 may include a plurality of antennas (e.g., array antennas). In such a case, at least one antenna appropriate for a communication scheme used in the communication network, such as the first network 298 or the second network 299, may be selected, for example, by the communication module 290 (e.g., the wireless communication module 292) from the plurality of antennas. The signal or the power may then be transmitted or received between the communication module 290 and the external electronic device via the selected at least one antenna. According to an embodiment, another component (e.g., a radio frequency integrated circuit (RFIC)) other than the radiating element may be additionally formed as part of the antenna module 297.

According to certain embodiments, the antenna module 297 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 201 and the external electronic device 204 via the server 208 coupled with the second network 299. Each of the electronic devices 202 or 204 may be a device of a same type as, or a different type, from the electronic device 201. According to an embodiment, all or some of operations to be executed at the electronic device 201 may be executed at one or more of the external electronic devices 202, 204, or 208. For example, if the electronic device 201 should perform a function or a service automatically, or in response to a request from a user or another device, the electronic device 201, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 201. The electronic device 201 may provide the outcome, with or without further processing of the outcome, as at least part of a reply to the request. To that end, a cloud computing, distributed computing, mobile edge computing (MEC), or client-server computing technology may be used, for example. The electronic device 201 may provide ultra-low-latency services using, e.g., distributed computing or mobile edge computing. In another embodiment, the external electronic device 204 may include an internet-of-things (IoT) device. The server 208 may be an intelligent server using machine learning and/or a neural network. According to an embodiment, the external electronic device 204 or the server 208 may be included in the second network 299. The electronic device 201 may be applied to intelligent services (e.g., smart home, smart city, smart car, or healthcare) based on 5G communication technology or IoT-related technology.

An electronic device 100 according to an embodiment of the disclosure may include a housing 110 including a front plate 111, a back plate 113 that faces the front plate 111, and a side frame 112 that surrounds a space between the front plate 111 and the back plate 113, a circuit board 140 disposed in the housing 110, and a module assembly 170 disposed between the circuit board 140 and the back plate 113 and electrically connected with the circuit board 140. The module assembly 170 may include an optical sensor module 160 including a flexible circuit board 161 (e.g., a flexible printed circuit board or "FPCB") including a first surface 161a and a second surface 161b that faces away from the first surface 161a, a light emitting part 162 disposed on the first surface 161a of the flexible circuit board 161, and a light receiving part 163 disposed on the first surface 161a so as to be spaced apart from the light emitting part 162, and a wireless charging module 150 disposed to surround the flexible circuit board 161 and at least partially coupled to the flexible circuit board 161 so as to be integrated with the flexible circuit board 161.

In certain embodiments, the flexible circuit board 161 may be electrically connected with the wireless charging module 150.

In certain embodiments, the light emitting part 162 and the light receiving part 163 may be disposed on the first surface 161a of the flexible circuit board 161 in a chip on board manner.

In certain embodiments, the wireless charging module 150 may include an opening 154 that is formed in a central area of the wireless charging module 150 and in which the flexible circuit board 161 is located and a connecting portion 153 coupled to the flexible circuit board 161, and the connecting portion 153 may extend toward the flexible circuit board 161 from a peripheral portion 155 that surrounds the opening 154.

In certain embodiments, the connecting portion 153 may be coupled to the flexible circuit board 161 through soldering.

In certain embodiments, the connecting portion 153 may be physically and electrically connected to the first surface 161a of the flexible circuit board 161.

In certain embodiments, the connecting portion 153 may overlap at least a portion of the first surface 161a of the flexible circuit board 161 when the first surface 161a of the flexible circuit board 161 is viewed from above.

In certain embodiments, the back plate 113 may include a rear case 114 coupled to the side frame 112 and a cover 115 coupled to the rear case 114, and the module assembly 170 may be located in a space between the rear case 114 and the cover 115 and may be coupled to the cover 115.

In certain embodiments, the optical sensor module 160 may further include a first sidewall 164 disposed on the first surface 161a to surround the light emitting part 162, and the light emitting part 162 may be disposed on a central area of the first surface 161a, the light receiving part 163 may be disposed to surround the light emitting part 162, and the first sidewall 164 may be disposed between the light emitting part 162 and the light receiving part 163.

In certain embodiments, the optical sensor module 160 may further include a second sidewall 165 disposed adjacent to a peripheral area of the first surface 161a and spaced apart from the first sidewall 164, and the first sidewall 164 and the second sidewall 165 may be attached to the cover 115.

In certain embodiments, the light emitting part 162 may emit light toward an external object through the cover 115, the light receiving part 163 may receive reflected light formed by reflection of the light emitted from the light emitting part 162 by the external object, and the optical sensor module 160 may be configured such that the light emitting part 162 is located in a predetermined space formed by the cover and the first sidewall 164 and incidence of light other than the reflected light on the light receiving part 163 may be limited.

In certain embodiments, the first sidewall 164 and the second sidewall 165 may protrude to a predetermined height from the first surface 161a of the flexible circuit board 161, and the cover 115 may be spaced apart from the light emitting part 162 and the light receiving part 163 by a specified distance G by the first sidewall 164 and the second sidewall 165.

In certain embodiments, the cover 115 may include a plurality of electrodes 1151, 1152, 1153, and 1154 disposed on a surface of the cover 115, the flexible circuit board 161 may include at least one hole 166 formed in an edge portion thereof and may be disposed such that the first surface 161a faces the cover 115, and a conductive material electrically connected with the plurality of electrodes 1151, 1152, 1153, and 1154 may be disposed in the hole 166.

In certain embodiments, the plurality of electrodes 1151, 1152, 1153, and 1154 may include an outside electrode 1151, 1152 located on the outside of the housing 110 and an inside electrode 1153, 1154 located inside the housing 110 and electrically connected with the outside electrode 1151, 1152. A portion of the inside electrode 1153, 1154 may be aligned with the hole 166 in a direction substantially perpendicular to the first surface 161a. The conductive material may fill the hole 166 to make electrical contact with the inside electrode 1153, 1154.

In certain embodiments, the cover 115 may be configured to be assembled to the rear case 114 in a state of being coupled with the module assembly 170.

In certain embodiments, the wireless charging module 150 may include a third surface 151 that faces the same direction as the first surface 161a of the flexible circuit board 161 and a fourth surface 152 that faces the same direction as the second surface 161b of the flexible circuit board 161, and the flexible circuit board 161 may be located between the third surface 151 and the fourth surface 152 when a section of the module assembly 170 is viewed.

In certain embodiments, a first virtual extension line L1 that extends in parallel from the first surface 161a of the flexible circuit board 161 and a second virtual extension line L2 that extends in parallel from the second surface 161b of the flexible circuit board 161 may be defined, and the flexible circuit board 161 may be aligned with the wireless charging module 150 such that the first extension line L1 and the second extension line L2 are located between the third surface 151 and the fourth surface 152 of the wireless charging module 150.

A wearable electronic device 100 according to an embodiment of the disclosure may include a housing 110 including a front surface that faces a first direction D1, a rear surface that faces a second direction D2 opposite to the first direction D1, and a side surface that surrounds a space between the front surface and the rear surface, a display 120 disposed in the housing 110 and visually exposed through the front surface, a circuit board 140 disposed in the housing 110, a module assembly 170 disposed between the circuit board 140 and the rear surface and electrically connected with the circuit board 140, and a connecting member 189 that connects the module assembly 170 and the circuit board. The module assembly 170 may include an optical sensor module 160 including a flexible circuit board 161 including a first surface 161a that faces the second direction D2 and a second surface 161b that faces the first direction D1, a light emitting part 162 disposed on the first surface 161a of the flexible circuit board 161, and a light receiving part 163 disposed on the first surface 161a so as to be spaced apart from the light emitting part 162, and a wireless charging module 150 disposed to surround the flexible circuit board 161 and at least partially coupled to the flexible circuit board 161 so as to be integrated with the flexible circuit board 161. The optical sensor module 160 may sense a biometric signal of an external object as the light emitting part 162 emits light in the second direction D2 and the light receiving part 163 receives light formed by reflection of the light emitted from the light emitting part 162 by the external object brought into contact with the rear surface of the electronic device 100.

In certain embodiments, the wireless charging module 150 may include an opening 154 that is formed in a central area of the wireless charging module 150 and in which the flexible circuit board 161 is located and a connecting portion 153 coupled to the flexible circuit board 161, and the connecting portion 153 may extend toward the flexible circuit board 161 from a peripheral portion 155 that surrounds the opening 154 and may be electrically connected with the flexible circuit board 161.

In certain embodiments, a connector 167 may be disposed on the second surface 161b of the flexible circuit board 161, and the connecting member 189 may be connected to the connector 167 and the circuit board 140.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with certain embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 240) including one or more instructions that are stored in a storage medium (e.g., internal memory 236 or external memory 238) that is readable by a machine (e.g., the electronic device 201). For example, a processor (e.g., the processor 220) of the machine (e.g., the electronic device 201) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities, and some of the multiple entities may be separately disposed in different components. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

What is claimed is:

1. An electronic device, comprising:
a housing including a front plate, a back plate facing the front plate, and a side frame surrounding a space defined between the front plate and the back plate;
a circuit board disposed within the housing; and
a module assembly disposed between the circuit board and the back plate, and electrically connected with the circuit board,
wherein the module assembly includes:
an optical sensor module including a flexible printed circuit board (FPCB) including a first surface and a second surface facing away from the first surface, a light emitting part disposed on the first surface of the FPCB, and a light receiving part disposed on the first surface spaced apart from the light emitting part, and
a wireless charging module surrounding the FPCB of the optical sensor module, and at least partially coupled to the FPCB so as to be integrated with the FPCB;
wherein the wireless charging module further includes a third surface facing a same direction as the first surface of the FPCB, and a fourth surface facing a same direction as the second surface of the FPCB; and
wherein the FPCB is disposed between the geometric planes extending the third surface and the fourth surface when a side section of the module assembly is viewed, and the side section is a section in a direction substantially perpendicular to the third surface or the fourth surface.

2. The electronic device of claim 1, wherein the FPCB is electrically connected to the wireless charging module.

3. The electronic device of claim 1, wherein the light emitting part and the light receiving part are disposed on the first surface of the FPCB in a chip-on-board (COB) manner.

4. The electronic device of claim 1, wherein the wireless charging module further includes an opening formed in a central area thereof, in which the FPCB is disposed, and a connecting portion coupled to the FPCB, and
wherein the connecting portion extends towards the FPCB from a peripheral portion surrounding the opening.

5. The electronic device of claim 4, wherein the connecting portion is coupled to the FPCB through soldering.

6. The electronic device of claim 4, wherein the connecting portion is physically and electrically connected to the first surface of the FPCB.

7. The electronic device of claim 6, wherein the connecting portion overlaps at least a portion of the first surface of the FPCB, when the first surface of the FPCB is viewed from above.

8. The electronic device of claim 1, wherein the back plate further includes a rear case coupled to the side frame, and a cover coupled to the rear case, and wherein the module assembly is disposed in a space defined between the rear case and the cover, and is coupled to the cover.

9. The electronic device of claim 8, wherein the optical sensor module further includes a first sidewall disposed on the first surface surrounding the light emitting part, and
wherein the light emitting part is disposed on a central area of the first surface,
wherein the light receiving part is disposed surrounding the light emitting part, and
wherein the first sidewall is disposed between the light emitting part and the light receiving part.

10. The electronic device of claim 9, wherein the optical sensor module further includes a second sidewall disposed adjacent to a peripheral area of the first surface, and is spaced apart from the first sidewall, and
wherein the first sidewall and the second sidewall are attached to the cover.

11. The electronic device of claim 9, wherein the light emitting part emits light towards an external object through the cover,
wherein the light receiving part receives emitted light that is reflected off the external object back towards the light receiving part, and
wherein the light emitting part is located in a predetermined space formed via the cover and the first sidewall, and an incidence of light other than the reflected light to the light receiving part is limited.

12. The electronic device of claim 10, wherein the first sidewall and the second sidewall protrude to a predetermined height from the first surface of the FPCB, and
wherein the cover is spaced apart from the light emitting part and the light receiving part by a specified distance, by the first sidewall and the second sidewall.

13. The electronic device of claim 10, wherein the cover includes a plurality of electrodes disposed on a surface of the cover,
wherein the FPCB includes at least one hole formed in an edge portion thereof, and is disposed such that the first surface faces the cover, and
wherein a conductive material electrically connected with the plurality of electrodes is disposed in the hole.

14. The electronic device of claim 13, wherein the plurality of electrodes includes an external electrode located on an exterior of the housing and an internal electrode located within the housing,
wherein the internal electrode is electrically connected with the external electrode,
wherein a portion of the internal electrode is aligned with the hole in a direction substantially perpendicular to the first surface, and
wherein the hole is filled with a conductive material in electrical contact with the internal electrode.

15. The electronic device of claim 8, wherein the cover is assemblable to the rear case when coupled with the module assembly.

16. The electronic device of claim 1, wherein the FPCB is coupled to the wireless charging module such that a first virtual line extending parallel to the first surface from a edge of the first surface, and a second virtual line extending parallel to the second surface from a edge of the second surface are disposed between the third surface and the fourth surface when the side section of the module assembly is viewed.

17. A wearable electronic device, comprising:
a housing including a front surface facing a first direction, a rear surface facing a second direction opposite to the first direction, and a side surface surrounding a space between the front surface and the rear surface;
a display disposed in the housing and visibly exposed through the front surface;
a circuit board disposed in the housing;
a module assembly disposed between the circuit board and the rear surface, and electrically connected with the circuit board; and
a connecting member connecting the module assembly and the circuit board,
wherein the module assembly includes:
an optical sensor module including a flexible printed circuit board (FPCB) including a first surface facing the second direction and a second surface facing the first direction, a light emitting part disposed on the first surface of the FPCB, and a light receiving part disposed on the first surface so as to be spaced apart from the light emitting part, and
a wireless charging module surrounding the FPCB and at least partially coupled to the FPCB so as to be integrated with the FPCB, and
wherein the optical sensor module is configured to detect a biometric signal of an external object as the light emitting part emits light in the second direction, and the light receiving part receives emitted light reflecting off the external object, when the external object is in contact with the rear surface of the wearable electronic device;
wherein the wireless charging module further includes a third surface facing a same direction as the first surface of the FPCB, and a fourth surface facing a same direction as the second surface of the FPCB; and
wherein the FPCB is disposed between the geometric planes extending the third surface and the fourth surface when a side section of the module assembly is viewed, and the side section is a section in a direction substantially perpendicular to the third surface or the fourth surface.

18. The wearable electronic device of claim 17, wherein the wireless charging module includes an opening that is formed in a central area thereof, and in which the FPCB and a connecting portion coupled to the FPCB are disposed, and
wherein the connecting portion extends towards the FPCB from a peripheral portion surrounding the opening, and is electrically connected with the FPCB.

19. The wearable electronic device of claim 17, wherein a connector is disposed on the second surface of the FPCB, and wherein the connecting member is connected to the connector and the FPCB.

* * * * *